United States Patent
Perkins et al.

(10) Patent No.: US 9,851,340 B2
(45) Date of Patent: Dec. 26, 2017

(54) INTEGRATED COMPUTATIONAL ELEMENTS WITH PLANAR WAVEGUIDE

(71) Applicant: Halliburton Energy Services, Inc., Houston, TX (US)

(72) Inventors: David L. Perkins, The Woodlands, TX (US); Christopher Michael Jones, Houston, TX (US); Nagaraja Pai, Houston, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 4 days.

(21) Appl. No.: 14/902,278

(22) PCT Filed: Sep. 19, 2014

(86) PCT No.: PCT/US2014/056645
§ 371 (c)(1),
(2) Date: Dec. 30, 2015

(87) PCT Pub. No.: WO2016/043777
PCT Pub. Date: Mar. 24, 2016

(65) Prior Publication Data
US 2016/0238585 A1    Aug. 18, 2016

(51) Int. Cl.
*G01N 33/28* (2006.01)
*E21B 47/10* (2012.01)
(Continued)

(52) U.S. Cl.
CPC ....... *G01N 33/2823* (2013.01); *E21B 47/102* (2013.01); *E21B 49/08* (2013.01);
(Continued)

(58) Field of Classification Search
CPC .................................................. G01N 33/2823
See application file for complete search history.

(56) References Cited

U.S. PATENT DOCUMENTS

| | | | | |
|---|---|---|---|---|
| 3,814,498 A | * | 6/1974 | Tomlinson, III | G02B 6/124 359/569 |
| 4,274,706 A | * | 6/1981 | Tangonan | G01J 3/0259 385/130 |

(Continued)

FOREIGN PATENT DOCUMENTS

WO    WO2007027073    3/2007

OTHER PUBLICATIONS

Babin et al., "Digital Optical Spectometer-on-chip," Applied Physics Letters 95, Apr. 11, 2005, DOI: 10.1063/1.3190199, Jul. 27, 2009, 3 pages.

(Continued)

*Primary Examiner* — Tarifur Chowdhury
*Assistant Examiner* — Omar Nixon
(74) *Attorney, Agent, or Firm* — Alan Bryson; Parker Justiss, P.C.

(57) ABSTRACT

In some implementations, optical analysis systems use an integrated computational element (ICE) that includes a planar waveguide configured as an ICE core. In other implementations, the ICE used by the disclosed optical analysis systems includes a planar waveguide configured as a spectrograph, the spectrograph to be integrated with a conventional ICE.

19 Claims, 12 Drawing Sheets

(51) Int. Cl.
*G01J 3/02* (2006.01)
*G01J 3/36* (2006.01)
*E21B 49/08* (2006.01)
*G01N 21/27* (2006.01)
*G01N 21/41* (2006.01)
*G01J 3/12* (2006.01)

(52) U.S. Cl.
CPC .............. *G01J 3/0205* (2013.01); *G01J 3/36* (2013.01); *G01N 21/27* (2013.01); *G01N 21/41* (2013.01); *E21B 2049/085* (2013.01); *G01J 2003/1226* (2013.01)

(56) References Cited

U.S. PATENT DOCUMENTS

| | | | |
|---|---|---|---|
| 5,347,375 | A | 9/1994 | Saito et al. |
| 5,615,008 | A | 3/1997 | Stachelek |
| 6,873,444 | B1 | 3/2005 | Guletsky et al. |
| 6,876,474 | B2 | 4/2005 | Kreuzer et al. |
| 7,330,614 | B1 | 2/2008 | Mossberger et al. |
| 7,423,748 | B2 | 9/2008 | Hagler |
| 7,729,579 | B1 | 6/2010 | Greiner et al. |
| 7,889,336 | B2 | 2/2011 | Yankov |
| 8,068,709 | B2 | 11/2011 | Iazikov et al. |
| 8,164,050 | B2 | 4/2012 | Ford et al. |
| 8,520,204 | B2 | 8/2013 | Desserouer |
| 2006/0055935 | A1 | 3/2006 | Cheben et al. |
| 2007/0046945 | A1 | 3/2007 | Schwiesow |
| 2008/0078544 | A1* | 4/2008 | Christian ................. G01J 3/02 166/264 |
| 2009/0073450 | A1 | 3/2009 | Boyd et al. |
| 2010/0009269 | A1 | 1/2010 | Davis et al. |
| 2010/0322558 | A1* | 12/2010 | Ogawa ............... G02B 6/12007 385/37 |
| 2011/0171773 | A1* | 7/2011 | Yang .................... G02B 6/0043 438/72 |
| 2012/0050735 | A1 | 3/2012 | Higgins et al. |
| 2012/0250120 | A1 | 10/2012 | Ostroverkhov et al. |
| 2013/0093936 | A1 | 4/2013 | Scheeline et al. |
| 2013/0208329 | A1 | 8/2013 | Harvill |
| 2014/0076550 | A1 | 3/2014 | Pelletier et al. |

OTHER PUBLICATIONS

Capraro, "Data Management for an Integrated Computational Environment," Capraro Technologies, Inc., RL-TR-97-70, Aug. 1997, 94 pages.
Halliburton, "Downhole Fluid Analysis with Lab-Quality Results—ICE Core Fluid Analysis Service," H010766, Sep. 2013, 5 pages.
Offshore Staff, "SPE 2013: Halliburton rolls out ICE Core downhole fluid analysis technology," Offshore Mag, Oct. 1, 2013, 3 pages, http://www.offshore-mag.com/articles/2013/10/spe-2013-halliburton-rolls-out-ice-core-downhole-fluid-analysis-technology.html.
PCT International Search Report and Written Opinion of the International Searching Authority, PCT/US2014/056645, dated Jun. 19, 2015, 13 pages.
Redding et al., "On-chip random spectrometer ," Department of Applied Physics, Yale University, New Haven, CT, published in 2013, 10 pages.

* cited by examiner

INTEGRATED COMPUTATIONAL ELEMENTS WITH PLANAR WAVEGUIDE

CROSS-REFERENCE TO RELATED APPLICATIONS

This application is a U.S. National Phase Patent Application under 35 U.S.C. §371 and claims the benefit of priority to International Application Serial No. PCT/US2014/056645, filed on Sep. 19, 2014, the contents of which are hereby incorporated by reference.

TECHNICAL FIELD

The subject matter of this disclosure is generally related to optical analysis systems for analyzing a substance of interest, for example, crude petroleum, gas, water, or other wellbore fluids. For example, the disclosed optical analysis systems use an integrated computational element (ICE) that includes a planar waveguide.

BACKGROUND

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

An ICE selectively weights, when operated as part of optical analysis tools, light modified by a sample in a processing wavelength range such that the weighted light is related to one or more chemical or physical characteristics of the sample. The ICE includes an ICE core which measures the various sample characteristics through the use of regression techniques and one or more band-limiting filters which limit the measured characteristics to the processing wavelength range. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

DESCRIPTION OF DRAWINGS

Like reference symbols in the various drawings indicate like elements.

DETAILED DESCRIPTION

Figure 1A:
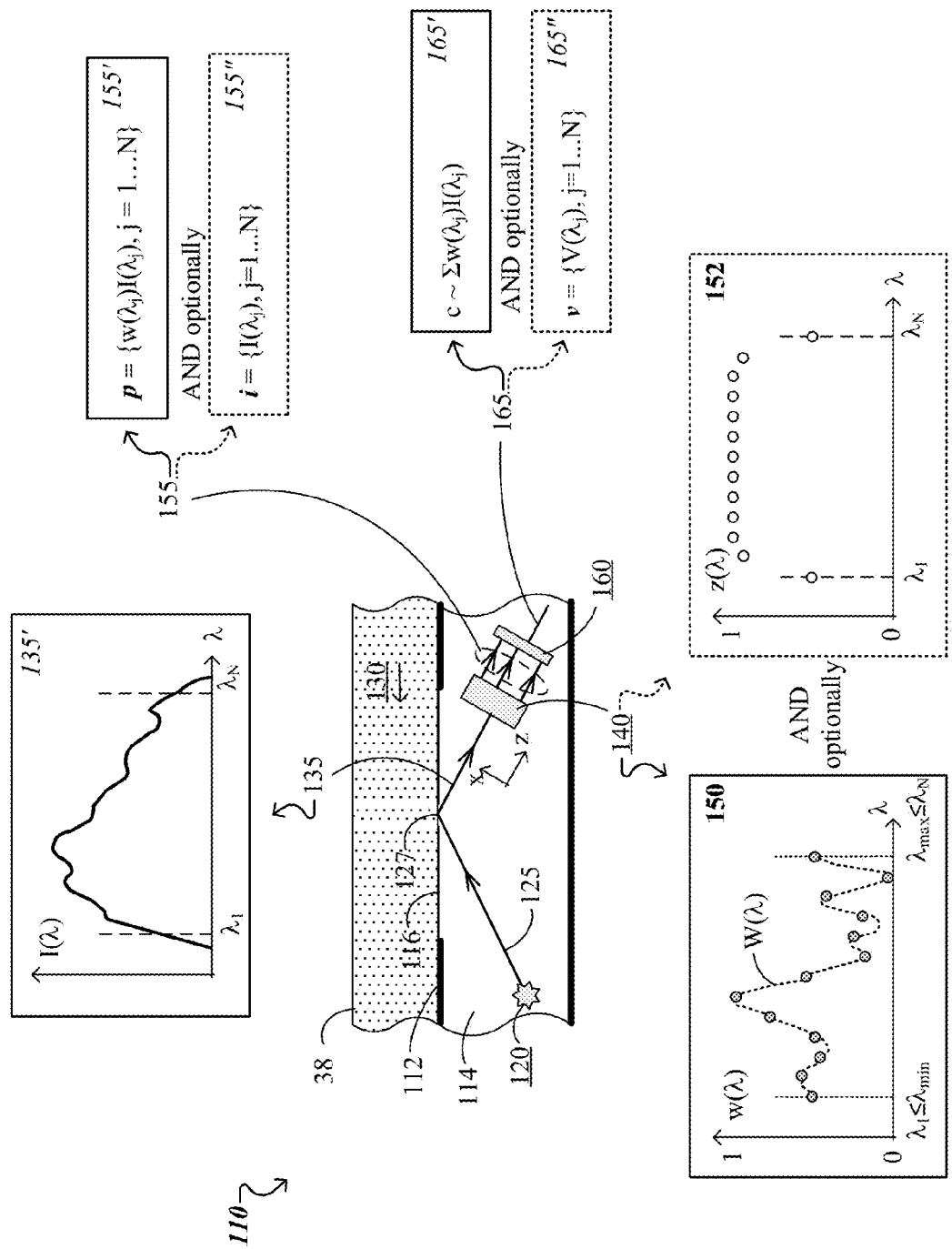
FIGS. 1A-1C show aspects of an optical analysis tool for measuring a characteristic of a sample using an ICE with a planar waveguide.

In accordance with the disclosed technologies, optical analysis systems use an ICE that includes a planar waveguide. Light input into the planar waveguide of the ICE is guided by the planar waveguide for wavelengths within an operational wavelength range $[\lambda_1, \lambda_N]$. Further, the planar waveguide spatially separates the guided light into N wavelength sub-ranges $\lambda_j$, where j=1 . . . N, of the operational wavelength range $[\lambda_1, \lambda_N]$, such that the spatially separated light can be output from the planar waveguide as different beams of light with wavelengths in the respective wavelength sub-ranges.

In some implementations, the planar waveguide of the ICE is configured as a spectrograph. Here, the planar waveguide-based spectrograph (PWS) weights the respective wavelength sub-ranges $\lambda_j$, where j=1 . . . N, of the spatially separated light by substantially equal amounts. In these implementations, the ICE further includes an ICE core that weights light incident thereof by differing amounts corresponding to the wavelength sub-ranges within a processing wavelength range $[\lambda_{min}, \lambda_{max}]$, where the different amounts are related to the characteristic of the sample. Here, $\lambda_1 \le \lambda_{min}$ and $\lambda_{max} \le \lambda_N$, such that a processing wavelength range $[\lambda_{min}, \lambda_{max}]$, of the ICE core is at most as large as the operational wavelength range $[\lambda_1, \lambda_N]$. For example, the operational wavelength range associated with the PWS can be 400-600 nm, and the processing wavelength range associated with the ICE core is 450-550 nm. As another example, the operational wavelength range associated with the PWS can be 400-600 nm, and the processing wavelength range associated with the ICE core also is 400-600 nm.

The ICE core can be an optical substrate with multiple stacked dielectric layers, each having a refractive index different from refractive indices of its adjacent layers. The specific number of layers, the optical properties of the layers, the optical properties of the substrate, and the physical thickness of each of the layers that compose the ICE core are selected so that the ICE core weights light incident thereof by differing amounts corresponding to the wavelength sub-ranges within the processing wavelength range $[\lambda_{min}, \lambda_{max}]$. Alternatively, the ICE core can include neutral density attenuators, acousto-optic elements, micro-electro-mechanical systems (MEMS) based devices or frequency selective surfaces that transmit, reflect, and/or absorb light incident thereof by differing amounts corresponding to the wavelength sub-ranges within the processing wavelength range $[\lambda_{min}, \lambda_{max}]$, where the different amounts are related to the characteristic of the sample.

The disclosed combination of PWS and ICE core can be implemented by placing the PWS upstream or downstream from the ICE core. Further, the disclosed combination of PWS and ICE core can be fabricated modularly or monolithically. Implementations of the combination of PWS and ICE core are described in detail below. Moreover, the PWS can be used to capture a spectrum of the light received from the sample within in the operational wavelength range of the PWS. In some cases, the spectrum is recorded along with the characteristic of the sample determined by the ICE core at a time when the spectrum of the sample modified light is captured. In this manner, correlations between the characteristic of the sample (as determined by the ICE core) and the spectrum of the sample modified light (as captured with the PWS) can be generated and/or refined.

In other implementations, the planar waveguide is configured as an ICE core. Here, the light input into the planar waveguide-based ICE core is received from a sample. Further here, $\lambda_{min}=\lambda_1$ and $\lambda_{max}=\lambda_N$, such that a processing wavelength range $[\lambda_{min}, \lambda_{max}]$ of the ICE core substantially coincides with the operational wavelength range $[\lambda_1, \lambda_N]$. For example, the operational wavelength range and the processing wavelength range associated with the PW-ICE core can be 400-600 nm. In this manner, the PW-ICE core weights the respective wavelength sub-ranges $\lambda_j$, where j= 1 ... N, of the spatially separated light by differing amounts corresponding to the wavelength sub-ranges, where the differing amounts are related to a characteristic of the sample. Typically, limiting an operational wavelength range of an ICE to a processing wavelength range of its ICE core is accomplished by placing a conventional band-pass optical filter in an optical path that includes (i) the sample, (ii) the ICE core that processes the light received from the sample and (iii) an optical transducer that detects the light processed by the ICE core and outputs a signal that is related to one or more characteristics of the sample. In contrast, the planar waveguide of the disclosed ICE configured as a PW-ICE core limits the operational wavelength range $[\lambda_1, \lambda_N]$ of the disclosed ICE to the processing wavelength range $[\lambda_{min}, \lambda_{max}]$ because the $\lambda_1=\lambda_{min}$ and $\lambda_N=\lambda_{max}$, by design.

In this manner, the disclosed ICE with planar waveguide configured as a PW-ICE core can be more compact and potentially may require reduced optical alignment complexity relative to ICEs having a combination of ICE core and conventional band-pass filter(s). In this manner, optical analysis systems based on the disclosed ICEs with planar waveguide configured as a PW-ICE core can be advantageously fabricated to be more compact and rugged than optical analysis systems based on ICEs having a combination of ICE core and conventional band-pass filter(s). As such, the disclosed ICEs with planar waveguide configured as a PW-ICE core can be utilized as part of permanent down-hole optical analysis systems. Additionally or alternatively, the disclosed ICEs with planar waveguide configured as a PW-ICE core can be utilized as part of dispersible optical analysis systems to be dispersed in a fluid system to collect data over time. For instance, such a dispersible optical analysis system can be inserted in wellbore fluid at a first depth below the ground level and it is later retrieved downstream from the first depth at a second depth below the ground level. Here, the second depth is between the first depth and the ground level if the wellbore fluid flows uphole or the first depth is between the second depth and the ground level if the wellbore fluid flows downhole. In some implementations, data collected by the dispersible optical analysis system can be analyzed in-situ, while the dispersible optical analysis system flows within the wellbore fluid from the first depth to the second depth. In other implementations, the data collected by the dispersible optical analysis system can be analyzed after the dispersible optical analysis system is retrieved at the second depth.

Moreover, an ICE with a planar waveguide configured as a PW-ICE core contains fewer optical interfaces relative to an ICE having a combination of ICE core and conventional band-pass filter(s). Hence, signal-to-noise ratios (SNR) of the disclosed ICEs with a planar waveguide configured as a PW-ICE core can advantageously be larger than the SNR of ICEs having a combination of ICE core and conventional band-pass filter(s).

Prior to describing example implementations of disclosed ICEs with a planar waveguide, optical analysis tools based on the disclosed ICEs are described below along with examples of their use in oil/gas exploration.

FIG. 1A shows an example of an optical analysis tool 110 for measuring a characteristic of a sample 130 using an ICE 140 with planar waveguide. In this example, the optical analysis tool 110 includes a light source 120, the ICE 140 with planar waveguide and an optical transducer 160. The optical analysis tool 110 has a frame 112 such that the foregoing components are arranged in an enclosure 114 thereof. A cross-section of the optical analysis tool 110 in a plane perpendicular to the page can vary, depending on the space available. For example, the optical analysis tool's cross-section can be circular or rectangular, for instance. The optical analysis tool 110 directs light to a sample 130 through an optical interface 116, e.g., a window in the frame 112. The optical analysis tool 110 is configured to probe the sample 130 (e.g., wellbore fluids stationary or flowing) in a wellbore 38 through the optical interface 116 and to determine an amount (e.g., a value) of a given characteristic (also referred to as a property to be measured) of the probed sample 130. The characteristic to be measured can be any one or more of multiple properties of the sample 130 including concentration of a given substance in the sample, a gas-oil-ratio (GOR), pH value, density, viscosity, etc.

The light source 120 outputs light with a source spectrum over a particular wavelength range. In some implementations, the source spectrum can have non-zero intensity over the entire or most of the particular wavelength range. In some implementations, the source spectrum extends through UV-vis (0.2-0.8 µm) and near-IR (0.8-2.5 µm) spectral ranges. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample 135 has a modified spectrum $I(\lambda)$ 135' over the particular wavelength range. In general, the modified spectrum $I(\lambda)$ 135' encodes information about multiple characteristics associated with the sample 130, and more specifically the encoded information relates to current values of the multiple characteristics. In the example illustrated in FIG. 1A, the modified spectrum 135' contains information about one or more characteristics of the wellbore fluids 130.

With continued reference to FIG. 1A, and the Cartesian coordinate system provided therein for reference, the ICE 140 with planar waveguide is arranged to receive a beam 135 of the sample modified light, and is configured to (i) process a portion of the sample modified light within a processing wavelength range $[\lambda_{min}, \lambda_{max}]$ and (ii) output a set 155 of beams of processed light that are spatially separated into some of wavelength sub-ranges $\lambda_j$, where j= 1 ... N, of an operational wavelength range $[\lambda_1, \lambda_N]$. The beam 135 of sample modified light can be incident along the z-axis on an input optical port of the ICE 140 with planar waveguide, and the set 155 of spatially separated beams of processed light is output along different directions within the (x,z)-plane—after transmission through the ICE 140 with planar waveguide—at respective output ports thereof corresponding to the respective wavelength sub-ranges.

In the example illustrated in FIG. 1A, the ICE 140 with planar waveguide includes an ICE core that weights, over the processing wavelength range $[\lambda_{min}, \lambda_{max}]$, some of the wavelength sub-ranges $\lambda_j$, where $j=1 \ldots N$, of the spatially separated light by differing amounts corresponding to the wavelength sub-ranges, where the differing amounts are related to a characteristic of the sample. This response of the ICE core to light incident thereon corresponds to a discrete optical spectrum $w(\lambda)$ 150 associated with the ICE core, represented in FIG. 1A by filled circles. In turn, the discrete optical spectrum $w(\lambda)$ 150 is an approximation of an optical spectrum $W(\lambda)$ associated with the ICE core, represented in FIG. 1A by dotted-curve.

The optical spectrum $W(\lambda)$ is determined offline by applying conventional processes to a set of calibration spectra $I(\lambda)$ of the sample which correspond to respective known values of the characteristic to be measured. As illustrated by optical spectrum $W(\lambda)$, optical spectra generally may include multiple local maxima (peaks) and minima (valleys) between $\lambda_{min}$ and $\lambda_{max}$. The peaks and valleys may have the same or different amplitudes. For instance, an optical spectrum $W(\lambda)$ can be determined through regression analysis of $N_C$ calibration spectra $I_j(\lambda)$ of a sample, where $j=1 \ldots N_C$, such that each of the calibration spectra $I_j(\lambda)$ corresponds to an associated known value of a given characteristic for the sample. A typical number $N_C$ of calibration spectra $I_j(\lambda)$ used to determine the optical spectrum $W(\lambda)$ through such regression analysis can be $N_C=10$, 40 or 100, for instance. The regression analysis outputs, within the $N_C$ calibration spectra $I_j(\lambda)$, a spectral pattern that is unique to the given characteristic. The spectral pattern output by the regression analysis can correspond to the optical spectrum $W(\lambda)$. In this manner, when a value of the given characteristic for the sample is unknown, a modified spectrum $I_U(\lambda)$ of the sample is acquired by interacting the probe beam 125 with the sample 130, then the modified spectrum $I_U(\lambda)$ is weighted by the ICE core of the ICE 140 with planar waveguide to determine a magnitude of the spectral pattern corresponding to the optical spectrum $W(\lambda)$ within the modified spectrum $I_U(\lambda)$. The determined magnitude is proportional to the unknown value of the given characteristic for the sample.

For example, the sample can be a mixture (e.g., the wellbore fluid 130) containing substances X, Y and Z, and the characteristic to be measured for the mixture is concentration $c_X$ of substance X in the mixture. In this case, $N_C$ calibration spectra $I_j(\lambda)$ were acquired for $N_C$ samples of the mixture having respectively known concentration values for each of the substances contained in the $N_C$ samples. By applying regression analysis to the $N_C$ calibration spectra $I_j(\lambda)$, a first spectral pattern that is unique to the concentration $c_X$ of the X substance can be detected (recognized), such that the first spectral pattern corresponds to a first optical spectrum $W_{CX}(\lambda)$ associated with a first ICE core, for example. Similarly, second and third spectral patterns that are respectively unique to concentrations $c_Y$ and $c_Z$ of the Y and Z substances can also be detected, such that the second and third spectral patterns respectively correspond to second and third optical spectra $W_{CY}(\lambda)$ and $W_{CZ}(\lambda)$ respectively associated with second and third ICE cores. In this manner, when a new sample of the mixture (e.g., the wellbore fluid 130) has an unknown concentration $c_X$ of the X substance, for instance, a modified spectrum $I_U(\lambda)$ of the new sample can be acquired by interacting the probe beam 125 with the mixture, then the modified spectrum $I_U(\lambda)$ is weighted with the first ICE core to determine a magnitude of the first spectral pattern within the modified spectrum $I_U(\lambda)$. The determined magnitude is proportional to the unknown value of the concentration $c_X$ of the X substance for the new sample.

The ICE core of the ICE 140 with planar waveguide can be implemented in various ways.

For example, the ICE core of the ICE 140 can be a conventional ICE core with which the optical spectrum $W(\lambda)$ is associated over a processing wavelength range $[\lambda_{min}, \lambda_{max}]$, as described in detail below in connection with FIG. 1C. In this case, the ICE 140 includes a combination of such a conventional ICE core and the planar waveguide. Here, the planar waveguide is implemented as a PWS (as described in detail below in connection with FIG. 1B) that weights, over an operational wavelength range $[\lambda_1 \leq \lambda_{min}, \lambda_{max} \leq \lambda_N]$, the respective wavelength sub-ranges $\lambda_j$, where $j=1 \ldots N$, of the spatially separated light by substantially the same amounts. This response of the PWS to light incident thereon corresponds to a discrete optical spectrum $z(\lambda)$ 152 associated with the PWS, represented in FIG. 1A by empty circles.

As another example, the ICE core can be implemented based on the planar waveguide of the ICE 140, as described in detail below in connection with FIG. 1B. Here, the planar waveguide of the ICE 140 is configured as a PW-ICE core with which the discrete optical spectrum $w(\lambda)$ 150 is associated.

Note that, when implemented as a PW-ICE core, the planar waveguide blocks guided light shorter than $\lambda_1 = \lambda_{min}$ and longer than $\lambda_N = \lambda_{max}$, such that processed light output by the ICE 140 into the set 155 of N spatially separated beams is limited to the wavelength range $[\lambda_{min}, \lambda_{max}]$ over which the optical spectrum $W(\lambda)$ or its discrete approximation $w(\lambda)$ 150 is associated with the characteristic to be measured. In this manner, contributions of the optical spectrum $I(\lambda)$ 135' of the sample modified light that are from wavelengths outside the processing wavelength range $[\lambda_1 = \lambda_{min}, \lambda_N = \lambda_{max}]$ are weighted to zero. Alternatively, when implemented as a PWS, the planar waveguide blocks guided light shorter than $\lambda_1$ and longer than $\lambda_N$. In this case, the ICE core is bandwidth limited (e.g., using monolithically or modularly coupled optical band pass filters) such that processed light output by the ICE 140 into some of the spatially separated beams of the set 155 are limited to the processing wavelength range $[\lambda_{min}, \lambda_{max}]$ over which the optical spectrum $W(\lambda)$ or its discrete approximation $w(\lambda)$ 150 is associated with the characteristic to be measured. In this manner, contributions of the optical spectrum $I(\lambda)$ 135' of the sample modified light that are from wavelengths within the wavelength ranges $[\lambda_1, \lambda_{min}]$ and $[\lambda_{max}, \lambda_N]$ are weighted to zero. Hence, in either implementation of the planar waveguide, analysis noise potentially caused by such "outside-of-band" contributions—which may not be associated with the characteristic to be measured can be reduced.

The set 155 of spatially separated beams of processed light output by the ICE 140 with planar waveguide has a discrete processed spectrum $p = \{w(\lambda_j)I(\lambda_j), j=1 \ldots N\}$ 155' over the processing wavelength range $[\lambda_{min}, \lambda_{max}]$, such that, for some wavelength sub-ranges $\lambda_j$, the discrete processed spectrum 155' represents a respective value $I(\lambda_j)$ of the modified spectrum $I(\lambda)$ 135' weighted by a corresponding value $w(\lambda_j)$ of the discrete optical spectrum $w(\lambda)$ 150 associated with the characteristic to be measured.

The set 155 of spatially separated beams of processed light is directed from the ICE 140 with planar waveguide to the optical transducer 160. Here, the optical transducer includes a multi-element detector arranged to detect the spatially separated beams of processed light 155. Moreover, the optical transducer 160 outputs a detector signal 165. In this case, a scalar value (e.g., a voltage) of the detector signal 165 is a sum of values of the processed spectrum 155' corresponding to some wavelength sub-ranges of the wavelength range [$\lambda_{min}$, $\lambda_{max}$] and is related to the unknown value "c" 165' of the characteristic to be measured for the sample 130.

In some implementations, the optical analysis tool 110 can include a second ICE core (not shown in FIG. 1) having a second optical spectrum $w_2(\lambda)$. Here, the second optical spectrum $w_2(\lambda)$ is associated, over a second processing wavelength range, with a second characteristic of the sample 130. Hence, a second processed spectrum represents the modified spectrum $I(\lambda)$ 135' weighted by the second optical spectrum $w_2(\lambda)$ over the second processing wavelength range, such that a second value of a second detector signal is related to a value of the second characteristic for the sample 130.

Moreover, in embodiments of the ICE 140 that include a combination of a conventional ICE core and a planar waveguide implemented as a PWS, the conventional ICE core can be temporarily deactivated from the ICE 140. When so, the sample modified light 135 interacts only with the PWS of the ICE 140. In this case, the set 155 of beams output by the ICE 140 with planar waveguide is a set of N beams of the sample modified light that are spatially separated into respective wavelength sub-ranges $\lambda_j$, where j=1 . . . N, of the operational wavelength range [$\lambda_1 \leq \lambda_{min}$, $\lambda_{max} \leq \lambda_N$]. As such, the set 155 of spatially separated beams of sample modified light—output by the ICE 140 with planar waveguide—has a discrete modified spectrum i={$I(\lambda_j)$, j=1 . . . N} 155" over the operational wavelength range [$\lambda_1 \leq \lambda_{min}$, $\lambda_{max} \leq \lambda_N$], such that, for each wavelength sub-range $\lambda_j$, the discrete modified spectrum 155" represents a respective value $I(\lambda_j)$ of the modified spectrum $I(\lambda)$ 135'. Here, the set 155 of N spatially separated beams of sample modified light is directed from the ICE 140 with planar waveguide to the multi-element detector of the optical transducer 160. Here, the detector signal 165 is output as a set of voltages v={$V(\lambda_j)$, j=1 . . . N} 165" representing a mapping of the discrete modified spectrum 155" over the operational wavelength range [$\lambda_1 \leq \lambda_{min}$, $\lambda_{max} \leq \lambda_N$]. In this manner, the ICE 140 with planar waveguide can optionally acquire a spectrum 165" of light modified by a substance 130 along with a value 165' of a characteristic of the substance.

In some implementations, the value 165' of the characteristic to be measured, and optionally the set of voltages 165" representing the spectrum of sample modified light measured concurrently with the value 165' of the characteristic, can be logged along with a measurement time, geo-location, and other metadata, for instance. In some implementations, the detector signal 165, which is related to a characteristic to be measured by the optical analysis tool 110 (and optionally to the spectrum of sample modified light measured concurrently with a value of the characteristic), can be used as a feedback signal to adjust the characteristic of the sample, to modify the sample or environmental conditions associated with the sample, as desired.

In the example illustrated in FIG. 1A, the ICE 140 with planar waveguide that is included in the optical analysis tool 110 is described generally as having an ICE core. Example implementations of the ICE core included in the ICE 140 with planar waveguide are described below.

Figure 1B:
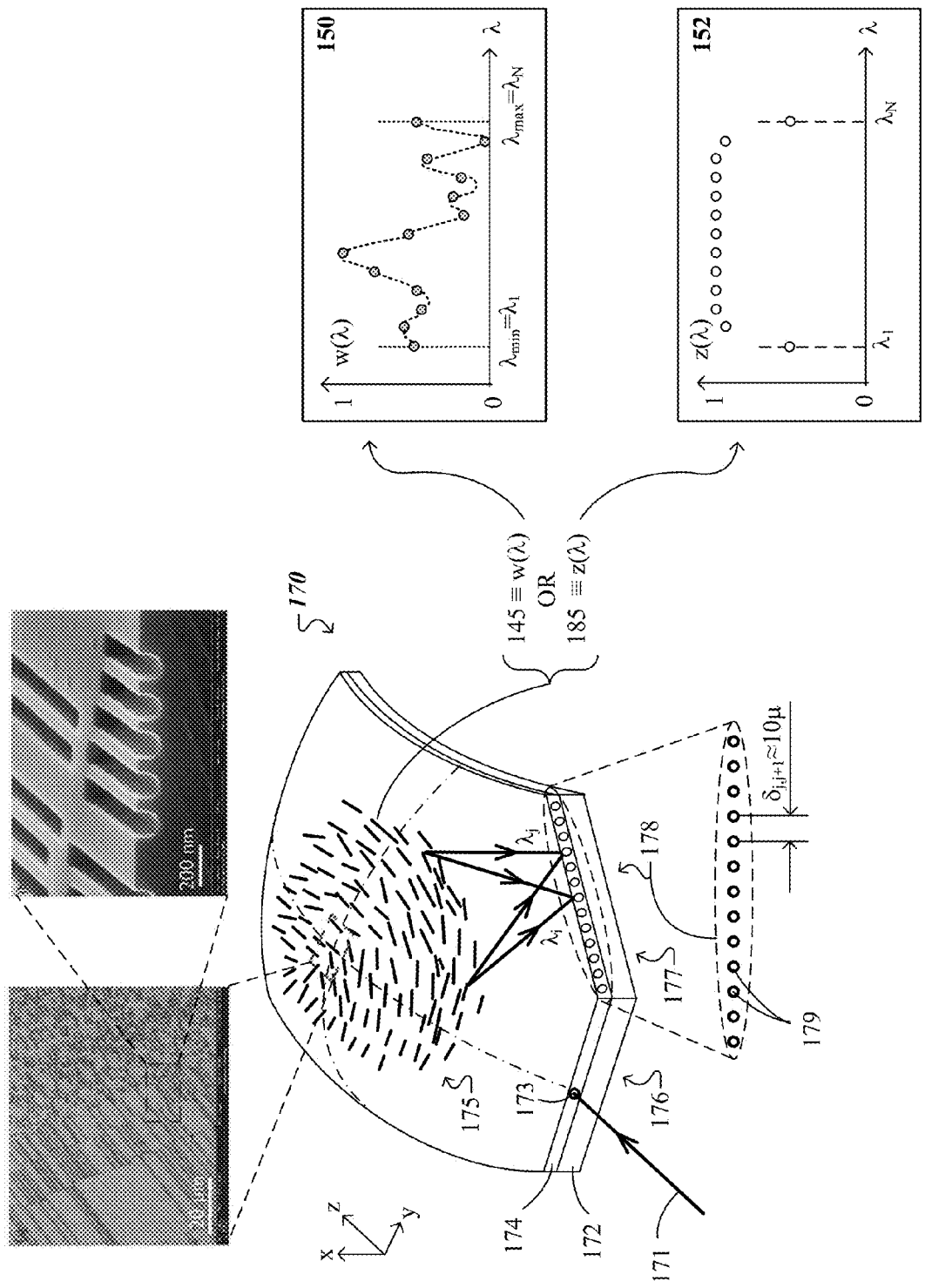

FIG. 1B shows aspects of a dispersive optical element 170 that is a component of the ICE 140 with planar waveguide.

The dispersive optical element 170 includes a substrate 172 and a planar waveguide 174 disposed on the substrate. An input port 173 located on an input facet 176 of the dispersive optical element 170 is used to receive input light 171. Diffractive structures 175 distributed along the planar waveguide 174 are used to spatially separate light guided through the planar waveguide into multiple wavelength sub-ranges of the wavelength range. N output ports 178 located on an output facet 177 of the dispersive optical element 170 are used to issue output light 179 in the form of N beams that are spatially separated into respective wavelength sub-ranges {$\lambda_j$, j=1 . . . N}.

The substrate can be made from $SiO_2$, for instance. A refractive index of the planar waveguide 174's material is chosen to be larger than a refractive index of the substrate 172's material. In some implementations, the planar waveguide 174 is made from Si so it guides light having wavelengths in the UV, visible or near-IR (with $\lambda < 1\mu$). In other implementations, the planar waveguide 174 is made from doped silica, e.g., $SiO_2Ge_X$ so it guides light with wavelengths extended into the mid-IR (with $\lambda < 3\mu$). In this manner, a combination of refractive indices of constitutive materials of the substrate 172 and planar waveguide 174 and thicknesses thereof limits wavelengths of the light guided through the planar waveguide to a desired operational wavelength range [$\lambda_1$, $\lambda_N$]. Depending on the embodiment, a thickness of the planar waveguide 174, e.g., the distance between a planar waveguide/air interface and a planar waveguide/substrate interface along the x-axis, is in the range of 0.1-100μ, e.g., about 0.2, about 0.5, about 1, about 2, about 5, about 10 or about 50μ. In-plane dimensions of the planar waveguide 174, e.g., length and width of the planar waveguide along the z- and y-axes, are in the range of 1-10 mm, e.g., about 2, about 3 or about 5 mm. The thickness of the planar waveguide 174 (e.g., along the x-axis) is uniform (within fabrication error) along the length and width thereof, such that the planar waveguide/air interface and the planar waveguide/substrate interface are parallel to each other. In some implementation, the planar waveguide 174 is flat, such that a curvature thereof is about zero (within measurement error.) In other implementations, the planar waveguide 174 is non-flat, such that the curvature thereof is finite (e.g., as shown in FIG. 1B by curved dash-dotted lines on the planar waveguide/air interface along the z- and y-axis.) It is noted that the curvature of a non-flat planar waveguide 174 is controlled to be less than a threshold curvature in order to sustain propagation of planar modes through the non-flat planar waveguide 174.

The diffractive structures 175 of the dispersive optical element 170 are refractive index altering features that can be lines or grooves etched at an interface between the planar waveguide 174 and the environment (e.g., air), for instance. Dimensions of the refractive index altering features are of order of a quarter of the wavelength(s) of the guided light to cause strong backscattering.

Moreover, the diffractive structures 175 are arranged (e.g., as shown in FIG. 1B in scanning electron microscope images taken at various magnifications) such that the received light is guided through the planar waveguide 174 along a path length L much longer ($10^3$ to $10^6$ longer) than wavelengths of the input light 171. For example, an arrangement of the diffractive structures 175 includes N sets of refractive index altering features. Each of the N sets can include a large quantity of refractive index altering features, e.g., $10^5$, $10^6$, etc., features. The features of each of the N sets extend over an associated direction in a plane (e.g., y-z) of the planar waveguide 174, such that a direction associate with each set of features is different from directions associated with other sets of features. Each of the N sets of refractive index altering features redirects guided light within an associated wavelength sub-range along an associated direction in the plane y-z, towards the output facet 177. Here, the light redirected within an associated wavelength sub-range, e.g., $\{\lambda_j, j=1 \ldots N\}$, exits the dispersive optical element 170 as output light 179 through an associated output port from among the N output ports 178. The number of output ports N of the dispersive optical element 170 can be N=4, 16, 64, 128, 256, 1024. Physical spacing $\delta_{i,j+1}$ between adjacent output ports can be from 1 to 50µ. Wavelength spacing between adjacent channels is typically about 1 nm or less.

In addition to causing the spatial separation of the N output beams 179 into respective wavelength sub-ranges $\{\lambda_j, j=1 \ldots N\}$ at corresponding output ports 178, the arrangement of the N sets of refractive index altering features also determines respective intensity values of the guided light redirected into respective wavelength sub-ranges $\{\lambda_j, j=1 \ldots N\}$.

For example, an arrangement 145 of the N sets of refractive index altering features causes the dispersive optical element 170 to output light with (i) a center wavelength $\lambda_{min}=\lambda_1$ and intensity $w(\lambda_{min}=\lambda_1)$ at the first output port; (ii) a center wavelength $\lambda_2$ and intensity $w(\lambda_2)$ at the second output port; (iii) a center wavelength $\lambda_3$ and intensity $w(\lambda_3)$ at the third output port; . . . ; (j) a center wavelength $\lambda_j$ and intensity $w(\lambda_j)$ at the $j^{th}$ output port; . . . ; and (N) a center wavelength $\lambda_{max}=\lambda_N$ and intensity $w(\lambda_{max}=\lambda_N)$ at the $N^{th}$ output port. This response of the dispersive optical element 170, represented in FIG. 1B by filled circles, corresponds to a discrete optical spectrum $w(\lambda)$ 150 related to a characteristic of a sample. In this manner, a configuration of the dispersive optical element 170 that includes arrangement 145 of the diffractive structures 175 can be used—in the ICE 140 of the optical analysis tool 110 described above in connection with FIG. 1A—as an ICE core to determine a value 165' of a characteristic of a sample 130. In this configuration of the dispersive optical element 170, the operational wavelength range $[\lambda_1, \lambda_N]$ of the ICE 140 coincides with the processing wavelength range $[\lambda_{min}, \lambda_{max}]$ of the ICE core, $[\lambda_1, \lambda_N]=[\lambda_{min}, \lambda_{max}]$.

As another example, an arrangement 185 of the N sets of refractive index altering features causes the dispersive optical element 170 to output light with (i) a center wavelength $\lambda_1 \leq \lambda_{min}$ and intensity $z(\lambda_1)$ at the first output port; (ii) a center wavelength $\lambda_2$ and intensity $z(\lambda_2)$ at the second output port; (iii) a center wavelength $\lambda_3$ and intensity $z(\lambda_3)$ at the third output port; . . . ; (j) a center wavelength $\lambda_j$ and intensity $z(\lambda_j)$ at the $j^{th}$ output port; . . . ; and (N) a center wavelength $\lambda_N \geq \lambda_{max}$ and intensity $z(\lambda_N)$ at the $N^{th}$ output port. This response of the dispersive optical element 170, represented in FIG. 1B by open circles, corresponds to a discrete optical spectrum $z(\lambda)$ 152 with flat intensity over most wavelength sub-ranges. For instance, intensity of the discrete optical spectrum $z(\lambda)$ 152 is substantially constant (e.g., within measurement error) for all but the first wavelength sub-range $\lambda_1$ and the $N^{th}$ wavelength sub-range $\lambda_N$. In these "edge" wavelength sub-ranges, a value of the intensity $z(\lambda_1)$ and/or $z(\lambda_N)$ may be 90%, 75%, 50%, 25% or 10% of a value of the intensity $z(\lambda_j)$, where $j \neq 1$ or N. In this manner, a configuration of the dispersive optical element 170 that includes arrangement 185 of the diffractive structures 175 can be used as a PWS in the ICE 140 of the optical analysis tool 110 described above in connection with FIG. 1A. A PWS having the discrete optical spectrum $z(\lambda)$ 152 can be used to acquire a spectrum 165" of light 135 modified by a sample 130. Alternatively, a PWS having the discrete optical spectrum $z(\lambda)$ 152 can be used in combination with a conventional ICE core—having an optical spectrum $W(\lambda)$ related to a characteristic of a sample 130 over a processing wavelength range $[\lambda_{min} \geq \lambda_1, \lambda_{max} \leq \lambda_N]$—to determine a value 165' of the characteristic of the sample.

Figure 1C:
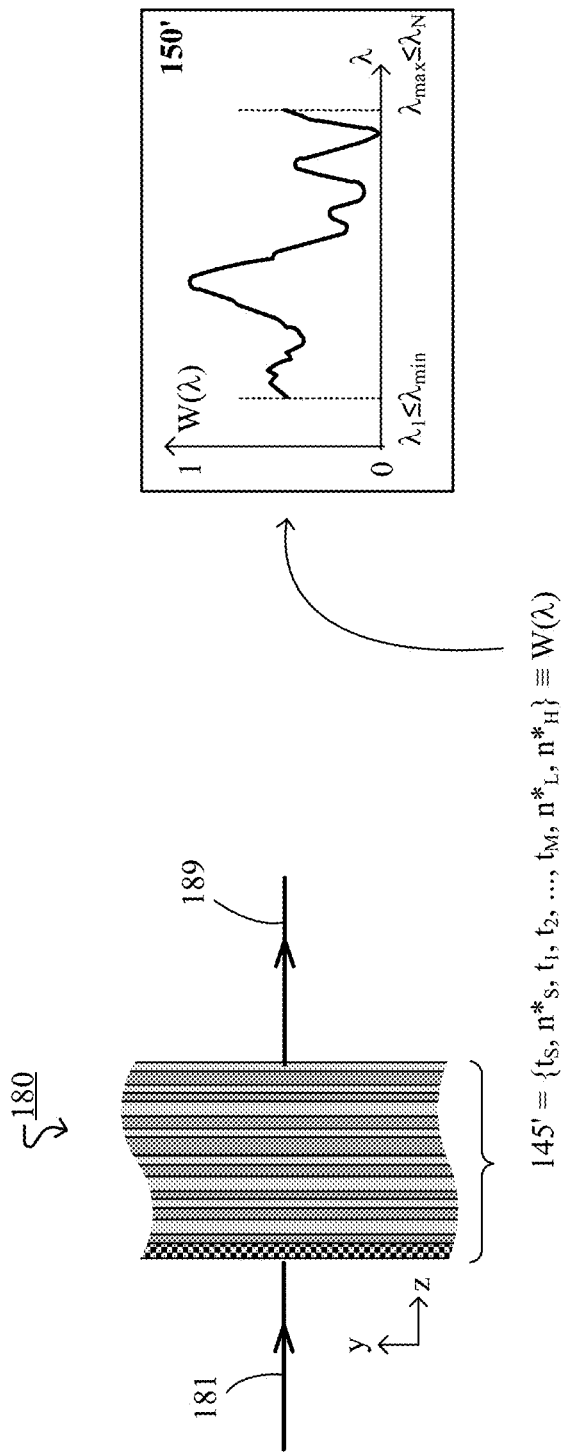

FIG. 1C shows aspects of such a conventional ICE core 180. Here, the conventional ICE core 180 includes M layers of materials stacked on a substrate, such that refractive indices of adjacent layers are different from each other. A set of design parameters 145 of the conventional ICE core 180—which here includes the total number M of stacked layers, the refractive indices of adjacent stacked layers, and the thicknesses of the M stacked layers—corresponds to an optical spectrum $W(\lambda)$ 150' associated with this embodiment of the conventional ICE core 180 over a processing wavelength range $[\lambda_{min}, \lambda_{max}]$. In this manner, a spectrum of output light 189 represents a spectrum of input light 181 weighted by the optical spectrum $W(\lambda)$ 150' associated with the conventional ICE core 180.

In other implementations, not shown in FIG. 1C, another conventional ICE core includes a layer of conductive material patterned as laterally-displaced periodic structures over a dielectric substrate, such that the patterned layer forms a frequency-selective surface (FSS). A set of design parameters of the other conventional ICE core—which here includes one or more of dimensions of lateral features of the FSS pattern, materials and thicknesses of the substrate and patterned layer, and one or more arrangements of the lateral features of the FSS pattern, e.g., triangular, rectangular, hexagonal or circular—corresponds to another optical spectrum associated with this embodiment of the other ICE core. In some other implementations, not shown in FIG. 1C, yet another conventional ICE core includes multiple spectral filters that are supported by a substrate and laterally-distributed relative to an input optical interface of the conventional ICE core. A set of design parameters of the other conventional ICE core—which here includes the total number of spectral filters and their relative areas—corresponds to yet another optical spectrum associated with this embodiment of the conventional ICE core.

Components of an ICE 140 with planar waveguide used in an optical analysis tool 110—for in-situ determining, e.g., downhole, a characteristic of wellbore fluids 130 concurrently with acquiring a spectrum of light modified by the wellbore fluids—were described above. Various embodiments of the optical analysis tool 110 are described next.

Figure 2:
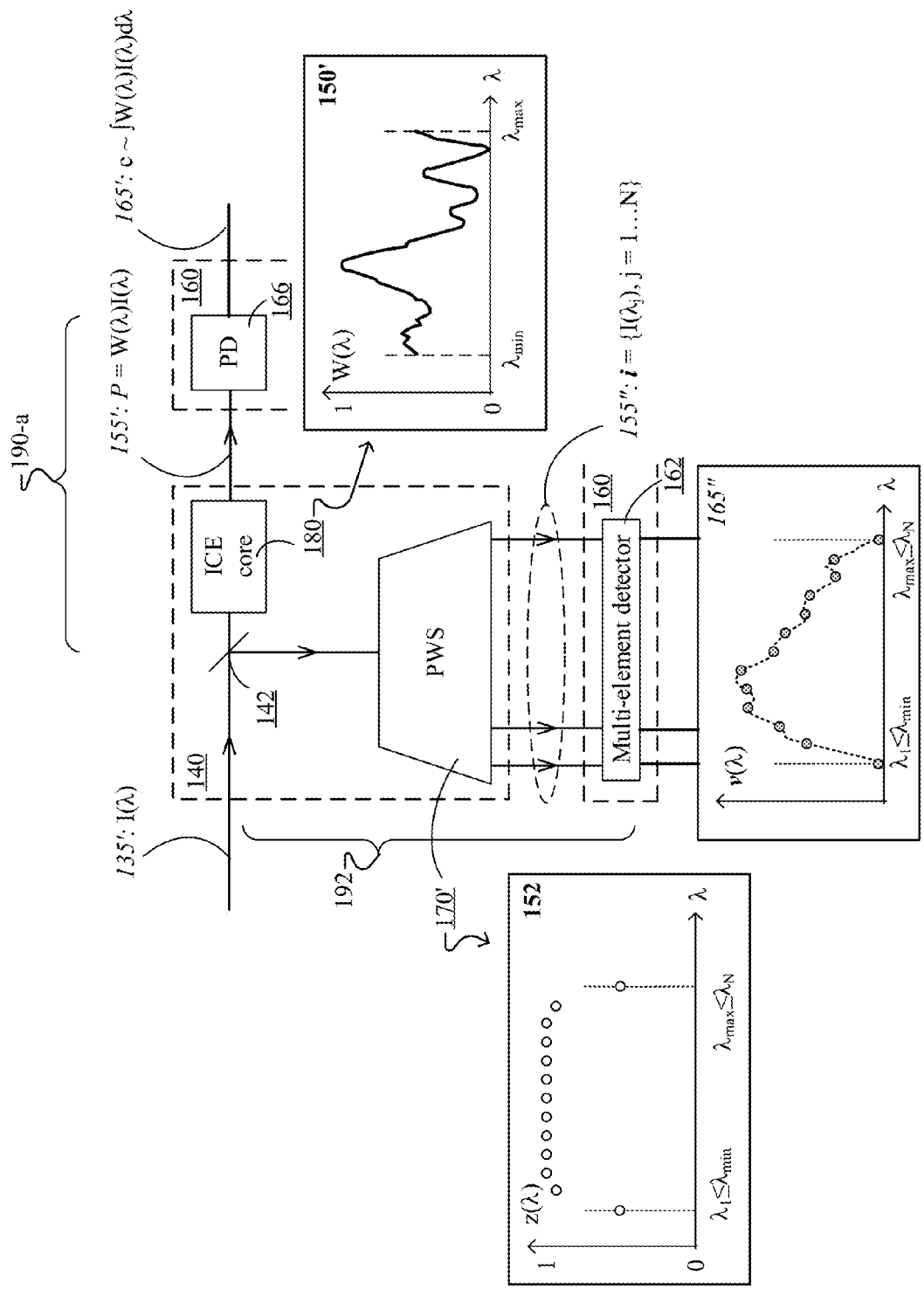
FIG. 2 shows a portion of an embodiment of an optical analysis tool with an ICE including an ICE core for measuring a characteristic of a sample and a planar waveguide-based spectrograph (PWS) for acquiring a spectrum of light modified by the sample.

FIG. 2 shows a portion of an optical analysis tool with an ICE 140 including an ICE core 180 for measuring a characteristic of a sample and a planar waveguide-based spectrograph (PWS) 170' for acquiring a spectrum of the sample. Here, the optical analysis tool also has an optical transducer 160 that includes a single-element detector 166 and a multi-element detector 162. The single-element detector 166 can be a photo-sensitive detector, e.g., a PIN diode. The multi-element detector 162 can be a linear array of photo-sensitive detectors, in some implementations. In other implementations, the multi-element detector 162 can be a charge-coupled device (CCD) or a complementary metal oxide semiconductor (CMOS)-based sensor. This optical analysis tool can be the optical analysis tool 110 described above in connection with FIG. 1A.

In the example illustrated in FIG. 2, the ICE 140 also includes a beam-splitter 142. The beam-splitter 142 directs a first portion of light modified by a sample to a computational branch 190-a of the optical analysis tool 110 and a remaining, second portion of the sample modified light to a spectrographic branch 192 of the optical analysis tool 110. The sample modified light has an unknown spectrum $I(\lambda)$ 135'. The computational branch 190-a—which includes the ICE core 180 and the single-element detector 166—is used to measure the characteristic of the sample from the first portion of the sample modified light. The spectrographic branch 192—which includes the PWS 170' and the multi-element detector 162—is used to acquire (and, optionally, record) the unknown spectrum $I(\lambda)$ 135' of the sample modified light from the second portion of the sample modified light.

Here, the ICE core 180 is a conventional ICE having an optical spectrum $W(\lambda)$ 150' related, over a processing wavelength range $[\lambda_{min}, \lambda_{max}]$, to the characteristic of the sample to be measured. Structure of the ICE core 180 is described above in connection with FIG. 1C. A band-pass optical filter (not shown in FIG. 2) is placed (modularly or monolithically) either between the beam-splitter 142 and the ICE core 180 or between the ICE core 180 and the optical transducer 160 to limit an operational wavelength range $[\lambda_1 \leq \lambda_{min}, \lambda_N \geq \lambda_{max}]$ of the ICE 140 to the processing wavelength range $[\lambda_{min}, \lambda_{max}]$ over which the optical spectrum $W(\lambda)$ 150' of the ICE core 180 relates to the characteristic of the sample. The ICE core 180 processes the sample modified light incident thereon by weighting the unknown spectrum $I(\lambda)$ 135' by the optical spectrum $W(\lambda)$ 150'. In this manner, a spectrum of the processed light is $P=W(\lambda)I(\lambda)$ 155'. The single-element detector 166 receives the processed light from the ICE core 180 and integrates the processed spectrum 155'. A value $\int W(\lambda)I(\lambda)d\lambda$. 165' of a detector signal output by the single-element detector 166 is proportional to a value c of the characteristic of the sample.

Further in the example illustrated in FIG. 2, the PWS 170' is a dispersive optical element having a discrete optical spectrum $z(\lambda)$ 152 over the operational wavelength range $[\lambda_1, \lambda_N]$. Structure of the PWS 170' is described above in connection with FIG. 1B, where the diffractive structures 175 of the PWS 170' are arranged in accordance with the arrangement 185. The PWS 170' receives the second portion of the sample modified light into an input port and outputs N beams of light at N output ports, respectively, where light output at the $j^{th}$ output port is sample modified light having wavelengths in a wavelength sub-range 4, where j=1 . . . N. In this manner, the set of N beams of sample modified light output at the N output ports of the PWS 170' has a discrete spectrum $i=\{I(\lambda_1), j=1 \ldots N\}$ 155'' over the operational wavelength range $[\lambda_1, \lambda_N]$, where, for each wavelength sub-range $\lambda_j$, the discrete modified spectrum 155'' represents a respective value $I(\lambda_j)$ of the unknown spectrum $I(\lambda)$ 135' of the sample modified light. For values of $z(\lambda)$ 152 that are less than unity, the discrete modified spectrum 155'' can be rescaled in post-processing such that the discrete modified spectrum 155'' matches that of the unknown spectrum 135'.

The multi-element detector 162 of the optical transducer 160 receives the N beams of sample modified light separated in respective wavelength sub-ranges $\{\lambda_j, j=1 \ldots N\}$ and outputs a detector signal including a set of voltages $v=\{V(\lambda_j), j=1 \ldots N\}$ 165'' corresponding to the respective wavelength sub-ranges $\{\lambda_j, j=1 \ldots N\}$. As the set of voltages 165'' represents a mapping of the discrete spectrum 155'' over the operational wavelength range $[\lambda_1, \lambda_N]$ of the sample modified light, it will be referred to as the acquired spectrum 165'' of the sample modified light.

In some implementations, the measured value 165' of the characteristic of the sample can be correlated with the acquired spectrum 165'' of the sample modified light in the following manner. Although not shown in FIG. 2, the optical analysis tool can include some recording medium (e.g., a storage device implemented as a memory buffer) and a comparator module. In some cases, one of or both the recording medium and comparator module is part of the optical analysis tool. Alternatively or additionally, one of or both the recording medium and comparator module is located remotely from the optical analysis tool, e.g., above the ground level, as described below in connection with FIGS. 9A-9C. Here, the recording medium and/or comparator module can be part of a computer associated with an oil rig or equipment auxiliary thereto. As another example, recording medium and/or comparator module can be part of computing devices disposed below the ground level, e.g., adjacent to casing collars that reinforce a borehole. The comparator module can be implemented as hardware, e.g., as an application-specific integrated circuit (ASIC), as firmware, as software, or a combination thereof.

Here, the comparator module compares the value 165' of the characteristic of the sample obtained at the output of the computational branch 190-a of the optical analysis tool with specified minimum and maximum values of the characteristic of the sample. The latter correspond to a dynamic range of a regression used to design and fabricate the ICE core 180.

In this manner, if the comparator module determines that the measured value 165' of the characteristic of the sample is bound by the specified minimum and maximum values, then the comparator module flags the measured value 165' as valid. A measured value 165' of the characteristic of the sample that is flagged as valid can be provided to a computer system (typically located remotely from the optical analysis tool, e.g., above or below the ground level) configured to monitor/control the sample, its environment, or both.

Alternatively, if the comparator module determines that the measured value 165' of the characteristic of the sample is smaller than the specified minimum value or larger than the specified maximum value, then the comparator module flags the measured value 165' as suspect. A measured value 165' of the characteristic of the sample that is flagged as suspect is recorded in the recording medium associated with the optical analysis tool along with the spectrum 165'' of the sample modified light acquired at the output of the spectrographic branch 192 of the optical analysis tool when the suspect value 165' was measured. The pair of the suspect value 165' of the characteristic of the sample and the spectrum 165'' of the sample modified light acquired when the suspect value 165' was measured can be provided to a computer system configured to perform corrective action(s). For example, if the computer system further determines that the suspect value 165' was measured with a measurement error that does not exceed a maximum allowed error, then the computer system can extend the dynamic range of the regression of the current ICE core 180. As another example, if the computer system further determines that the suspect value 165' was measured with a measurement error that exceeds the maximum allowed error, then the computer system can refine the dynamic range of the regression of the current ICE core 180. In this manner, the extended or refined regression dynamic range can be used to design and fabricate improved ICE cores for measuring the characteristic of the sample.

There are other instances when the acquired spectrum of the sample modified light is desired to be recorded in the recording medium at the same time when the sample characteristic is being measured. For example, the spectrum 165'' of the sample modified light acquired downhole can be compared (in-real time or in post-production) to spectra associated with a database of spectra used to design the ICE core 180. If the comparison shows the spectrum 165" is not in the database of spectra, then it can be added to the database of spectra for later use. In such cases, the value 165' of the characteristic of the sample measured when the spectrum 165" was acquired can be flagged as a suspect value. As another example, the spectrum 165" acquired downhole and stored in the recording medium as described herein can be compared to a sample modified spectrum acquired in a laboratory using simulated downhole conditions. Such comparisons can be used for quality assurance purposes or when there is reason to believe the fluid downhole may not be represented in a database associated with downhole fluids.

In the implementation 190-a of the computational branch of the optical analysis tool, the ICE 140 includes a conventional ICE core 180—e.g., like the one described above in connection with FIG. 1C—and the optical transducer 160 includes a single-element detector 166. Other implementations of the computational branch of the optical analysis tool are described below.

Figure 3A:
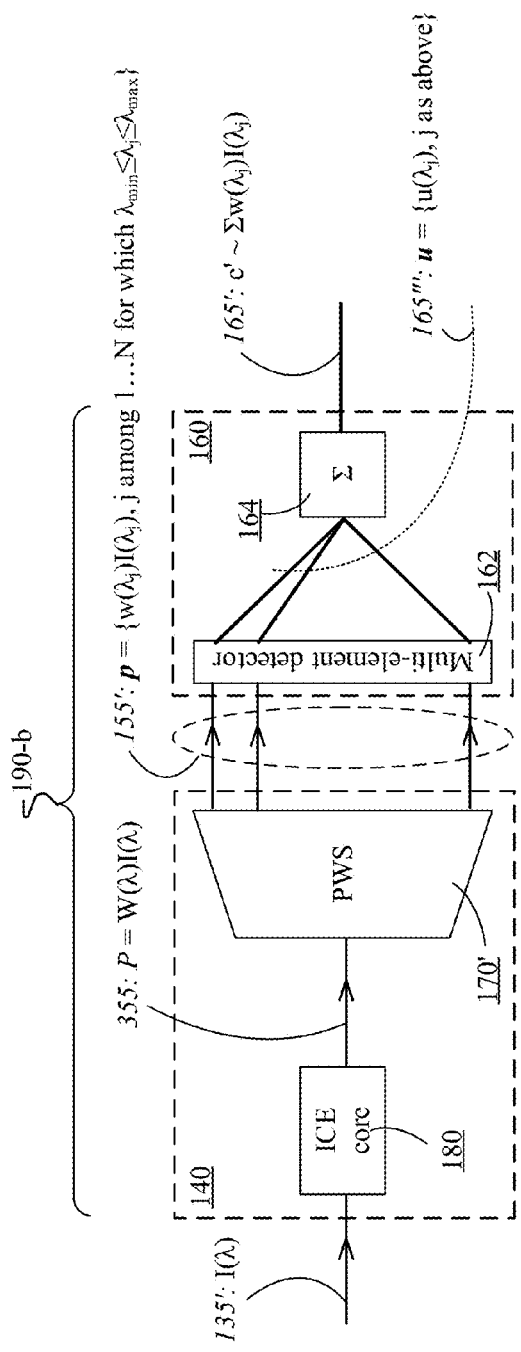
FIGS. 3A-3B and 4 show aspects of an optical analysis tool with an ICE including a combination of an ICE core and a PWS for measuring a characteristic of a sample, where the ICE core is disposed upstream from the PWS.

FIG. 3A shows a computational branch 190-b of an optical analysis tool with an ICE 140 including a combination of an ICE core 180 and a planar waveguide-based spectrograph (PWS) 170' for measuring a characteristic of a sample. In this combination, the ICE core 180 is disposed upstream from the PWS 170'. For example, the computational branch 190-b can be included in the optical analysis tool 110 described above in connection with FIG. 1A. As another example, the computational branch 190-b can be used in conjunction with the spectrographic branch 192 as described above in connection with FIG. 2, e.g., by simply replacing the computational branch 190-a illustrated in FIG. 2 with the computational branch 190-b illustrated in FIG. 3A. In addition to the ICE 140, the computational branch 190-b further includes an optical transducer 160 with a combination of a multi-element detector 162 and a summing module 164.

Here, the ICE core 180 is a conventional ICE having an optical spectrum $W(\lambda)$ 150' related, over a processing wavelength range $[\lambda_{min}, \lambda_{max}]$, to the characteristic of the sample to be measured. Structure of the ICE core 180 is described above in connection with FIG. 1C. The PWS 170' is a dispersive optical element having a discrete optical spectrum $z(\lambda)$ 152 over an operational wavelength range $[\lambda_1 \leq \lambda_{min}, \lambda_N \geq \lambda_{max}]$. Structure of the PWS 170' is described above in connection with FIG. 1B, where the diffractive structures 175 of the PWS 170' are arranged in accordance with the arrangement 185.

At an input end of the computational branch 190-b of an optical analysis tool, the ICE core 180 receives light modified by a sample. The sample modified light has an unknown spectrum $I(\lambda)$ 135'. The ICE core 180 processes the sample modified light incident thereon by weighting the unknown spectrum $I(\lambda)$ 135' by the optical spectrum $W(\lambda)$ 150'. In this manner, a spectrum of the processed light is $P = W(\lambda)I(\lambda)$ 355 over the processing wavelength range $[\lambda_{min}, \lambda_{max}]$. The PWS 170' receives the light processed by the ICE core 180 into an input port and outputs beams of processed light at some of N output ports. At such a $j^{th}$ output port where an output processed beam is issued, the processed light has wavelengths in an associated wavelength sub-range $\lambda_j$ for which $[\lambda_{min} \leq \lambda_j \leq \lambda_{max}]$. In this manner, the set of beams of processed light output at some of the N output ports of the PWS 170' has a discrete processed spectrum $p = \{w(\lambda_j)I(\lambda_j),$ with j being in a subset of 1 ... N for which $\lambda_{min} \leq \lambda_j \leq \lambda_{max}\}$ 155', where, for each wavelength sub-range $\lambda_j$, the discrete processed spectrum 155' represents a respective value $I(\lambda_j)$ of the unknown spectrum $I(\lambda)$ 135' of the sample modified light weighted by a corresponding value $w(\lambda_j)$ of the optical spectrum $W(\lambda)$ 150' associated with the characteristic to be measured.

In the example illustrated in FIG. 3A, the multi-element detector 162 of the optical transducer 160 receives the beams of processed light separated in respective wavelength sub-ranges $\lambda_j$, where j is in a subset of 1 ... N for which $\lambda_{min} \leq \lambda_j \leq \lambda_{max}$, and outputs an intermediary detector signal including a set of voltages $u = \{u(\lambda_j),$ with j being in a subset of 1 ... N for which $\lambda_{min} \leq \lambda_j \leq \lambda_{max}\}$ 165''' corresponding to the wavelength sub-ranges $\lambda_j$ within the processing wavelength range $[\lambda_{min}, \lambda_{max}]$. The set of voltages 165''' represents a mapping of the discrete processed spectrum 155' over the processing wavelength range $[\lambda_{min}, \lambda_{max}]$ of the processed light. The summing module 164 adds the voltages $u(\lambda_j)$ corresponding to the respective wavelength sub-ranges $\lambda_j$, where j is in a subset of 1 ... N for which $\lambda_{min} \leq \lambda_j \leq \lambda_{max}$, and outputs a detector signal. At an output end of the computational branch 190-b, a value $\Sigma w(\lambda_j)I(\lambda_j)$ 165' of a signal output by the summing module 164 is proportional to a value c' of the characteristic of the sample.

The ICE core 180 of the ICE 140 can be decoupled from and then recoupled to the input port of the PWS 170' using a switch—not shown in FIG. 3A. For example, the switch can be an optical switch, e.g., electro-mechanical shutter, acusto-optic modulator, scanning mirrors, etc. In this case, the ICE core 180 can be supported by a fixed mount (e.g., base, support, etc.) and the optical switch is used in conjunction with steering optics to direct the switched light to the input port of the PWS 170'. As another example, the switch can be implemented as a movable mount on which the ICE core 180 of the ICE 140 is being supported. The movable mount (e.g., a rotation or a translation stage, etc.) is moved by engaging one or more actuators, for instance. In either of these implementations of the switch, the ICE core 180 can be illuminated by a sample modified light having the unknown spectrum $I(\lambda)$ 135' for a finite time interval, e.g., 0.1, 0.5, 1 or 5 sec. For the sake of simplicity, the following applications are described for cases when the switch is implemented as a movable mount.

In some implementations, the movable mount also supports a second ICE core having another optical spectrum $W_2(\lambda)$ related, over a second processing wavelength range, to a second characteristic of the sample to be measured. After the finite time interval, the movable mount is moved such that the sample modified light having the unknown spectrum $I(\lambda)$ 135' now illuminates the second ICE core. In this manner, at the output end of the computational branch 190-b, a second value $\Sigma w_2(\lambda_j)I(\lambda_j)$ of the signal output by the summing module 164 is proportional to a value $c'_2$ of the second characteristic of the sample. As such, the movable mount is used to toggle between (i) a first state of the ICE 140 in which the ICE core 180 is coupled to and the second ICE core is decoupled from the input port of the PWS 170' and (ii) a second state of the ICE 140 in which the second ICE core is coupled to and the ICE core 180 is decoupled from the input port of the PWS 170'. In general, the movable mount can support $K \geq 2$ ICE cores having respective optical spectra $W_k(\lambda)$, where k=2 ... K, related, over an associated wavelength range, to a $k^{th}$ characteristic of the sample to be measured. In this manner, the movable mount can be used to cycle between K states of the ICE 140 in which a $k^{th}$ ICE core is coupled to the input port of the PWS 170'.

Figure 3B:
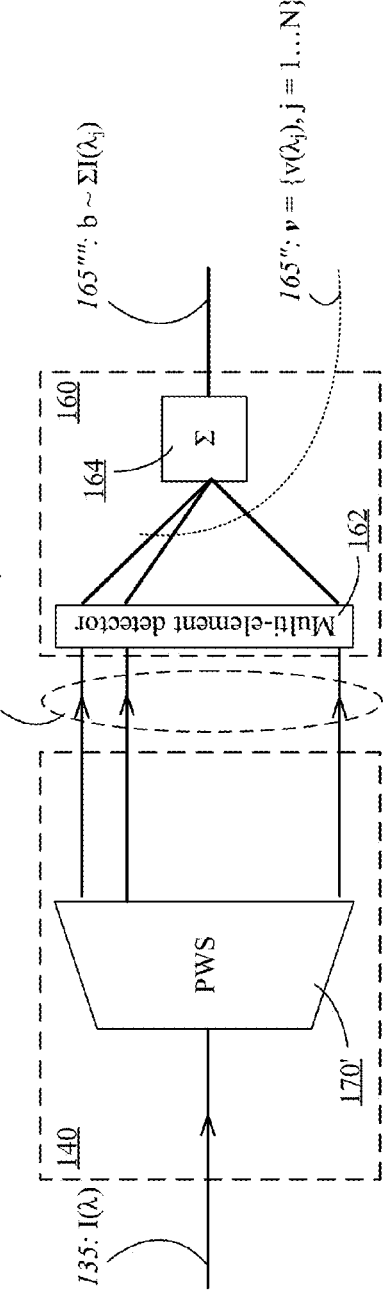

In some implementations, the movable mount has a transparent region (e.g., an aperture) such that the sample modified light having the unknown spectrum I(λ) 135' is transmitted through the transparent region without being weighted by the ICE core 180 (or any other ICE core supported by the mount.) FIG. 3B shows a state of the ICE 140 when the sample modified light having the unknown spectrum I(λ) 135' illuminates the transparent region of the movable mount. At the input end of the computational branch 190-b, the PWS 170' receives the sample modified light having the unknown spectrum I(λ) 135' into an input port and outputs N beams of light at N output ports, respectively. Here, the sample modified light output at the $j^{th}$ output port has wavelengths in an associated wavelength sub-range $\lambda_j$, where j=1 . . . N, within the operational wavelength range $[\lambda_1 \leq \lambda_{min}, \lambda_N \leq \lambda_{max}]$. In this manner, the set of N beams of sample modified light output at the N output ports of the PWS 170' has a discrete spectrum i={I($\lambda_j$), j=1 . . . N} 155" over the operational wavelength range $[\lambda_1, \lambda_N]$, where, for each wavelength sub-range $\lambda_j$, the discrete modified spectrum 155" represents a respective value I($\lambda_j$) of the unknown spectrum I(λ) 135' of the sample modified light. The multi-element detector 162 of the optical transducer 160 receives the N beams of sample modified light separated in respective wavelength sub-ranges {$\lambda_j$, j=1 . . . N} and outputs another intermediary detector signal including another set of voltages v={v($\lambda_j$), j=1 . . . N} 165" corresponding to the respective wavelength sub-ranges {$\lambda_j$, j=1 . . . N}. The set of voltages 165" represents a mapping of the discrete spectrum 155" over the operational wavelength range $[\lambda_1, \lambda_N]$ of the sample modified light. The summing module 164 adds the voltages v($\lambda_j$) corresponding to the respective wavelength sub-ranges {$\lambda_j$, j=1 . . . N} from the set 165" and outputs another detector signal. At the output end of the computational branch 190-b, a value ΣI($\lambda_j$) 165''' of another signal output by the summing module 164 is proportional to a normalizing value b. The normalizing value b can be used to normalize the value c' of the characteristic of the sample measured in the state of the ICE 140 when the sample modified light having the unknown spectrum I(λ) 135' illuminates the ICE core 180, as described in connection with FIG. 3A.

As such, the movable mount is used to toggle between a first state of the ICE 140 (shown in FIG. 3A) in which the ICE core 180 is coupled to the input port of the PWS 170' and a second state of the ICE 140 (shown in FIG. 3B) in which the ICE core 180 is decoupled from the input port of the PWS 170' and the sample modified light having the unknown spectrum I(λ) 135' is input directly to the input port of the PWS 170'.

Moreover, in implementations of the optical analysis tool 110 in which the computational branch 190-b illustrated in FIGS. 3A-3B is used without the spectroscopic branch 192 illustrated in FIG. 2, the set of voltages v={v($\lambda_j$), j=1 . . . N} 165" of the intermediary detector signal also can be output as an additional detector signal that maps the discrete spectrum 155" of the sample modified light over the operational wavelength range $[\lambda_1, \lambda_N]$.

Figure 4:
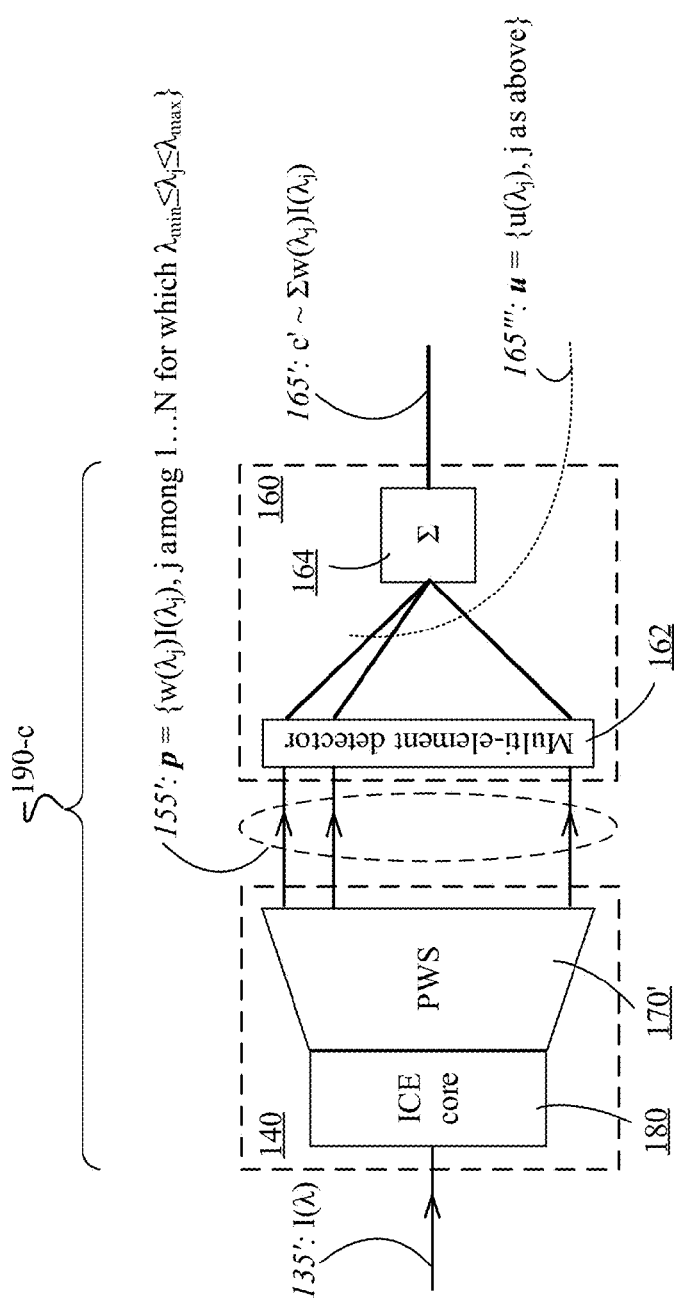

FIG. 4 shows another computational branch 190-c of an optical analysis tool with an ICE 140 including a combination of an ICE core 180 and a planar waveguide-based spectrograph (PWS) 170' for measuring a characteristic of a sample. In this other combination, the ICE core 180 is disposed on an input facet of the PWS 170'. For example, the computational branch 190-c can be included in the optical analysis tool 110 described above in connection with FIG. 1A. As another example, the computational branch 190-c can be used in conjunction with the spectrographic branch 192 as described above in connection with FIG. 2, e.g., by simply replacing the computational branch 190-a illustrated in FIG. 2 with the computational branch 190-c illustrated in FIG. 4. In addition to the ICE 140, the computational branch 190-c further includes an optical transducer 160 with a combination of a multi-element detector 162 and a summing module 164.

Here, the ICE core 180 is a conventional ICE having an optical spectrum W(λ) 150' related, over a processing wavelength range $[\lambda_{min}, \lambda_{max}]$, to the characteristic of the sample to be measured. Structure of the ICE core 180 is described above in connection with FIG. 1C. The PWS 170' is a dispersive optical element having a discrete optical spectrum z(λ) 152 over an operational wavelength range $[\lambda_1 \leq \lambda_{min}, \lambda_N \geq \lambda_{max}]$. Structure of the PWS 170' is described above in connection with FIG. 1B, where the diffractive structures 175 of the PWS 170' are arranged in accordance with the arrangement 185. In the implementation 190-c of the computational branch, the ICE core 180 is integrally formed on (e.g., directly deposited over) an input port of the PWS 170'.

At an input end of the computational branch 190-c of an optical analysis tool, the ICE core 180 receives light modified by a sample. The sample modified light has an unknown spectrum I(λ) 135'. The ICE core 180 processes the sample modified light incident thereon—by weighting the unknown spectrum I(λ) 135' by the optical spectrum W(λ) 150'—and provides processed light over the processing wavelength range $[\lambda_{min}, \lambda_{max}]$ into an input port of the PWS 170'. The PWS 170' outputs beams of processed light at some of N output ports. At such a $j^{th}$ output port where an output processed beam is issued, the processed light has wavelengths in an associated wavelength sub-range $\lambda_j$ for which $[\lambda_{min} \leq \lambda_j \leq \lambda_{max}]$. In this manner, the set of beams of processed light output at some of the N output ports of the PWS 170' has a discrete processed spectrum p={w($\lambda_j$)I($\lambda_j$), with j being in a subset of 1 . . . N for which $\lambda_{min} \leq \lambda_j \leq \lambda_{max}$} 155', where, for each wavelength sub-range $\lambda_j$, the discrete processed spectrum 155' represents a respective value I($\lambda_j$) of the unknown spectrum I(λ) 135' of the sample modified light weighted by a corresponding value w($\lambda_j$) of the optical spectrum W(λ) 150' associated with the characteristic to be measured.

The multi-element detector 162 of the optical transducer 160 receives the beams of processed light separated in respective wavelength sub-ranges $\lambda_j$, where j is in a subset of 1 . . . N for which $\lambda_{min} \leq \lambda_j \leq \lambda_{max}$, and outputs an intermediary detector signal including a set of voltages u={u($\lambda_j$), with j being in a subset of 1 . . . N for which $\lambda_{min} \leq \lambda_j \leq \lambda_{max}$} 165''' corresponding to the wavelength sub-ranges $\lambda_j$ within the processing wavelength range $[\lambda_{min}, \lambda_{max}]$. The set of voltages 165''' represents a mapping of the discrete processed spectrum 155' over the processing wavelength range $[\lambda_{min}, \lambda_{max}]$ of the processed light. The summing module 164 adds the voltages u($\lambda_j$) corresponding to the respective wavelength sub-ranges $\lambda_j$, where j is in a subset of 1 . . . N for which $\lambda_{min} \leq \lambda_j \leq \lambda_{max}$, and outputs a detector signal. At an output end of the computational branch 190-c, a value Σw($\lambda_j$)I($\lambda_j$) 165' of a signal output by the summing module 164 is proportional to a value c' of the characteristic of the sample.

Moreover, in implementations of the optical analysis tool 110 in which the computational branch 190-c illustrated in FIG. 4 is used without the spectroscopic branch 192 illustrated in FIG. 2, the set of voltages u={u($\lambda_j$), with j being in a subset of 1 . . . N for which $\lambda_{min} \leq \lambda_j \leq \lambda_{min}$} 165''' of the intermediary detector signal also can be output as an additional detector signal that maps the discrete processed spectrum 155' over the processing wavelength range $[\lambda_{min}, \lambda_{max}]$ of the processed light. In this manner, the voltages $u(\lambda_j)$ corresponding to the respective wavelength sub-ranges $\lambda_j$, where j is in a subset of 1 . . . N for which $\lambda_{min} \leq \lambda_j \leq \lambda_{max}$, can be used in combination with the known values $w(\lambda_j)$ of the ICE core spectrum 150 over the processing wavelength range $[\lambda_{min}, \lambda_{max}]$ to determine the discrete spectrum i={I($\lambda_j$), with j being in a subset of 1 . . . N for which $\lambda_{min} \leq \lambda_j \leq \lambda_{max}$} 155" of the sample modified light over the processing wavelength range $[\lambda_{min}, \lambda_{max}]$. As p=w*i, the processed spectrum 155' is multiplied by the inverse of the ICE core spectrum 150 to obtain the sample modified spectrum: $w^{-1} * p = w^{-1} * (w*i) = (w^{-1}*w)*i = i$. Hence, a set of voltages v={v($\lambda_j$), with j being in a subset of 1 . . . N for which $\lambda_{min} \leq \lambda_j \leq \lambda_{max}$} 165" that maps the discrete spectrum 155" of the sample modified light over the processing wavelength range $[\lambda_{min}, \lambda_{max}]$ is determined as $v(\lambda_j) = w^{-1}(\lambda_j)u(\lambda_j)$, for each sub-wavelength range $\lambda_j$, where j is in a subset of 1 . . . N for which $\lambda_{min} \leq \lambda_j \leq \lambda_{max}$.

Figure 5:
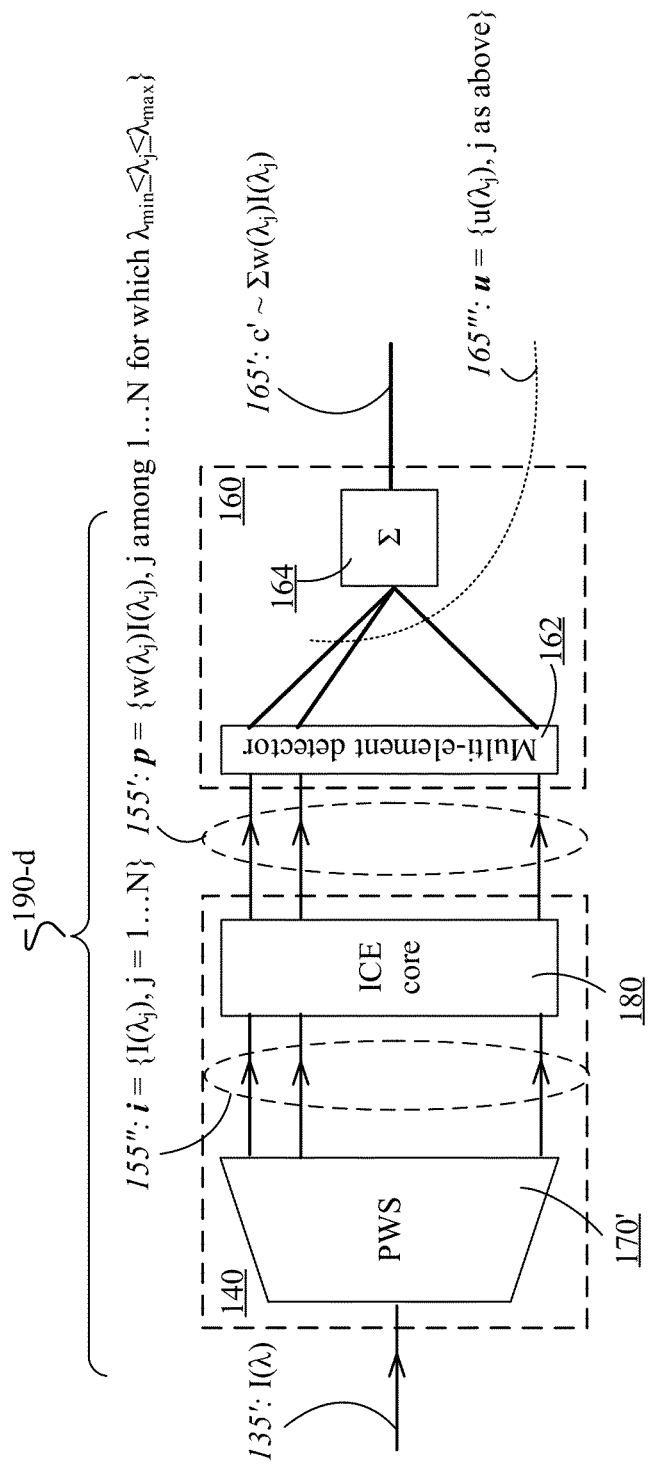
FIGS. 5, 6 and 7A-7B show aspects of an optical analysis tool with an ICE including a combination of an ICE core and a PWS for measuring a characteristic of a sample, where the ICE core is disposed downstream from the PWS.

FIG. 5 shows a computational branch 190-d of an optical analysis tool with an ICE 140 including a combination of an ICE core 180 and a planar waveguide-based spectrograph (PWS) 170' for measuring a characteristic of a sample. In this combination, the ICE core 180 is disposed downstream from the PWS 170'. For example, the computational branch 190-d can be included in the optical analysis tool 110 described above in connection with FIG. 1A. As another example, the computational branch 190-d can be used in conjunction with the spectrographic branch 192 as described above in connection with FIG. 2, e.g., by simply replacing the computational branch 190-a illustrated in FIG. 2 with the computational branch 190-d illustrated in FIG. 5. In addition to the ICE 140, the computational branch 190-d further includes an optical transducer 160 with a combination of a multi-element detector 162 and a summing module 164.

Here, the ICE core 180 is a conventional ICE having an optical spectrum W($\lambda$) 150' related, over a processing wavelength range $[\lambda_{min}, \lambda_{max}]$, to the characteristic of the sample to be measured. Structure of the ICE core 180 is described above in connection with FIG. 1C. The PWS 170' is a dispersive optical element having a discrete optical spectrum z($\lambda$) 152 over an operational wavelength range $[\lambda_1 \leq \lambda_{min}, \lambda_N \leq \lambda_{max}]$. Structure of the PWS 170' is described above in connection with FIG. 1B, where the diffractive structures 175 of the PWS 170' are arranged in accordance with the arrangement 185.

At an input end of the computational branch 190-d of an optical analysis tool, the PWS 170' receives, at an input port thereof, light modified by a sample. The sample modified light has an unknown spectrum I($\lambda$) 135'. The PWS 170' outputs N beams of sample modified light at N output ports, respectively, such that the sample modified light output at the $j^{th}$ output port has wavelengths in an associated wavelength sub-range $\lambda_j$, where j=1 . . . N. In this manner, the set of N beams of sample modified light output at the N output ports of the PWS 170' has a discrete spectrum i={I($\lambda_j$), J=1 . . . N} 155" over the operational wavelength range $[\lambda_1, \lambda_N]$, where, for each wavelength sub-range $\lambda_j$, the discrete modified spectrum 155" represents a respective value I($\lambda_j$) of the unknown spectrum I($\lambda$) 135' of the sample modified light. The set of N beams of sample modified light output at the N output ports of the PWS 170' is received by the ICE core 180. The ICE core 180 processes some the N beams of sample modified light by weighting the discrete modified spectrum 155" by the optical spectrum W($\lambda$) 150' within the processing wavelength range $[\lambda_{min}, \lambda_{max}]$ and blocks the remaining ones of the N beams that have sample modified light with wavelength within $[\lambda_1, \lambda_{min}]$ and $[\lambda_{max}, \lambda_N]$. In this manner, the set of beams of processed light output by the ICE core 180 has a discrete processed spectrum p={w($\lambda_j$)I ($\lambda_j$), with j being in a subset of 1 . . . N for which $\lambda_{min} \leq \lambda_j \leq \lambda_{max}$} 155', where, for each wavelength sub-range $\lambda_j$, the discrete processed spectrum 155' represents a respective value I($\lambda_j$) of the unknown spectrum I($\lambda$) 135' of the sample modified light weighted by a corresponding value w($\lambda_j$) of the optical spectrum W($\lambda$) 150' associated with the characteristic to be measured.

In the example illustrated in FIG. 5, the multi-element detector 162 of the optical transducer 160 receives the beams of processed light separated in respective wavelength sub-ranges $\lambda_j$, where j is in a subset of 1 . . . N for which $\lambda_{min} \leq \lambda_j \leq \lambda_{max}$, and outputs an intermediary detector signal including a set of voltages u={u($\lambda_j$), with j being in a subset of 1 . . . N for which $\lambda_{min} \leq \lambda_j \leq \lambda_{max}$} 165'" corresponding to the wavelength sub-ranges $\lambda_j$ within the processing wavelength range $[\lambda_{min}, \lambda_{max}]$. The set of voltages 165'" represents a mapping of the discrete processed spectrum 155' over the processing wavelength range $[\lambda_{min}, \lambda_{max}]$ of the processed light. The summing module 164 adds the voltages u($\lambda_j$) corresponding to the respective wavelength sub-ranges $\lambda_j$, where j is in a subset of 1 . . . N for which $\lambda_{min} \leq \lambda_j \leq \lambda_{max}$, and outputs a detector signal. At an output end of the computational branch 190-d, a value $\Sigma w(\lambda_j)I(\lambda_j)$ 165' of a signal output by the summing module 164 is proportional to a value c' of the characteristic of the sample.

The ICE core 180 of the ICE 140 can be decoupled from and then recoupled to the N output ports of the PWS 170' using a switch—not shown in FIG. 5. For example, the switch can be an optical switch, e.g., electro-mechanical shutter, acousto-optic modulator, scanning mirrors, etc. In this case, the ICE core 180 can be supported by a fixed mount (e.g., base, support, etc.) and the optical switch is used in conjunction with steering optics to direct the switched light from the N output ports of the PWS 170' to the multi-element detector 162 of the optical transducer 160. As another example, the switch can be implemented as a movable mount on which the ICE core 180 of the ICE 140 is being supported. The movable mount (e.g., a rotation or a translation stage, etc.) is moved by engaging one or more actuators, for instance. In either of these implementations of the switch, the ICE core 180 can be illuminated by N beams of sample modified light having the discrete spectrum i={I ($\lambda_j$), j=1 . . . N} 155" over the operational wavelength range $[\lambda_1, \lambda_N]$ for a finite time interval, e.g., 0.1, 0.5, 1 or 5 sec. For the sake of simplicity, the following applications are described for cases when the switch is implemented as a movable mount.

In some implementations, the movable mount also supports a second ICE core having another optical spectrum $W_2(\lambda)$ related, over a second processing wavelength range, to a second characteristic of the sample to be measured. After the finite time interval, the movable mount is moved such that the N beams of sample modified light having the discrete spectrum 155" now illuminates the second ICE core. In this manner, at the output end of the computational branch 190-d, a second value $\Sigma w_2(\lambda_j)I(\lambda_j)$ of the signal output by the summing module 164 is proportional to a value $c'_2$ of the second characteristic of the sample. As such, the movable mount is used to toggle between (i) a first state of the ICE 140 in which the ICE core 180 is coupled to and the second ICE core is decoupled from the N output ports of the PWS 170' and (ii) a second state of the ICE 140 in which the second ICE core is coupled to and the ICE core 180 is decoupled from the N output ports of the PWS 170'. In general, the movable mount can support K≥2 ICE cores having respective optical spectra $W_k(\lambda)$, where k=2 . . . K, related, over an associated wavelength range, to a $k^{th}$ characteristic of the sample to be measured. In this manner, the movable mount can be used to cycle between K states of the ICE 140 in which a $k^{th}$ ICE core is coupled to the N output ports of the PWS 170'.

In some implementations, the movable mount has a transparent region (e.g., an aperture) such that the N beams of sample modified light output at the N output ports of the PWS 170' are transmitted through the transparent region without being weighted by the ICE core 180 (or any other ICE core supported by the mount.) Reference is again made to FIG. 3B which shows a state of the ICE 140 when the N beams of sample modified light output at the N output ports of the PWS 170' illuminate the transparent region of the movable mount. Here, the set of N beams of sample modified light output at the N output ports of the PWS 170' has a discrete spectrum i={$I(\lambda_j)$, j=1 . . . N} 155" over the operational wavelength range [$\lambda_1 \leq \lambda_{min}$, $\lambda_N \geq \lambda_{max}$], where, for each wavelength sub-range $\lambda_j$, the discrete modified spectrum 155" represents a respective value $I(\lambda_j)$ of the unknown spectrum $I(\lambda)$ 135' of the sample modified light. The multi-element detector 162 of the optical transducer 160 receives the N beams of sample modified light separated in respective wavelength sub-ranges {$\lambda_j$, j=1 . . . N} and outputs another intermediary detector signal including another set of voltages v={$v(\lambda_j)$, j=1 . . . N} 165" corresponding to the respective wavelength sub-ranges {$\lambda_j$, j= 1 . . . N}. The set of voltages 165" represents a mapping of the discrete spectrum 155" over the operational wavelength range [$\lambda_1$, $\lambda_N$] of the sample modified light. The summing module 164 adds the voltages $v(\lambda_j)$ corresponding to the respective wavelength sub-ranges {$\lambda_j$, j=1 . . . N} from the set 165" and outputs another detector signal. At the output end of the computational branch 190-d, a value $\Sigma I(\lambda_j)$ 165"" of another signal output by the summing module 164 is proportional to a normalizing value b. The normalizing value can be used to normalize the value c' of the characteristic of the sample measured in the state of the ICE 140 when the N beams of sample modified light output at the N output ports of the PWS 170' illuminate the ICE core 180, as described in connection with FIG. 5.

As such, the movable mount is used to toggle between a first state of the ICE 140 (shown in FIG. 5) in which the ICE core 180 is coupled to the output ports of the PWS 170' and a second state of the ICE 140 (shown in FIG. 3B) in which the ICE core 180 is decoupled from the output ports of the PWS 170' and the N beams of sample modified light output at the N output ports of the PWS 170' are provided directly to the multi-element detector 162 of the optical transducer 160.

Moreover, in implementations of the optical analysis tool 110 in which the computational branch 190-d illustrated in FIGS. 5 and 3B is used without the spectroscopic branch 192 illustrated in FIG. 2, the set of voltages v={$v(\lambda_j)$, j=1 . . . N} 165" of the intermediary detector signal also can be output as an additional detector signal that maps the discrete spectrum 155" of the sample modified light over the operational wavelength range [$\lambda_1$, $\lambda_N$].

Figure 6:
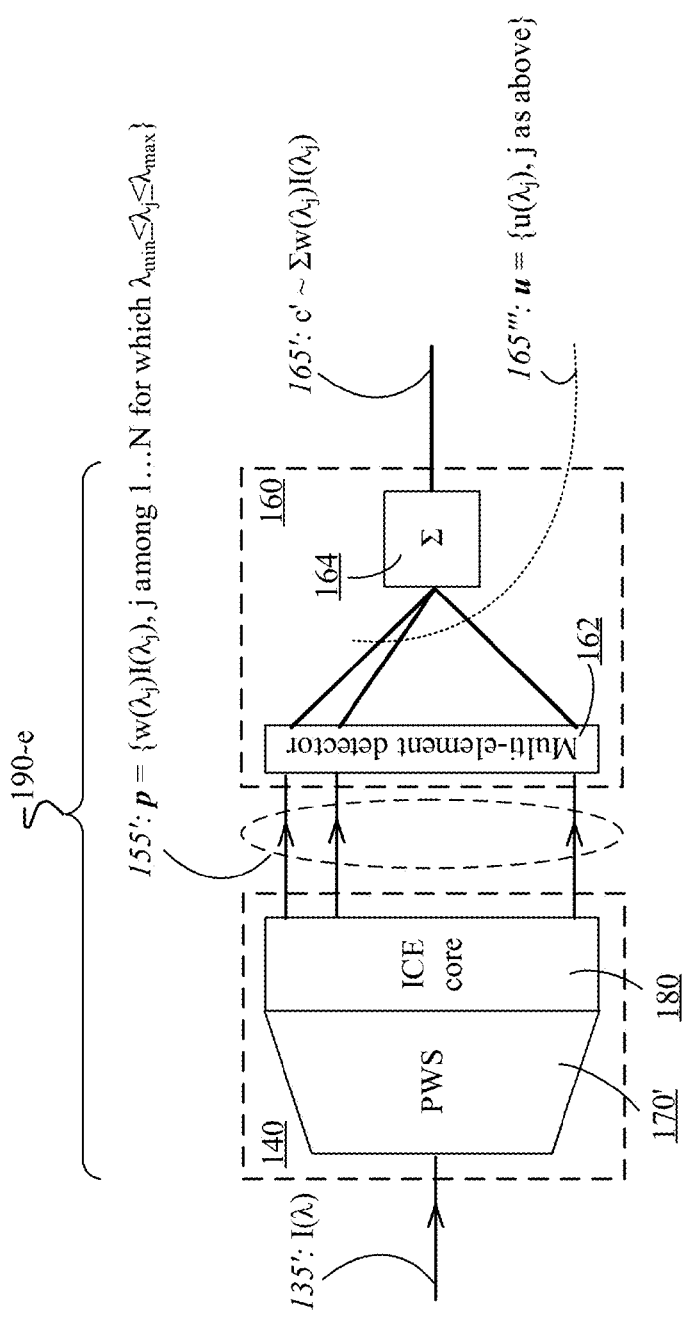

FIG. 6 shows another computational branch 190-e of an optical analysis tool with an ICE 140 including a combination of an ICE core 180 and a planar waveguide-based spectrograph (PWS) 170' for measuring a characteristic of a sample. In this other combination, the ICE core 180 is disposed on an output facet of the PWS 170'. For example, the computational branch 190-e can be included in the optical analysis tool 110 described above in connection with FIG. 1A. As another example, the computational branch 190-e can be used in conjunction with the spectrographic branch 192 as described above in connection with FIG. 2, e.g., by simply replacing the computational branch 190-a illustrated in FIG. 2 with the computational branch 190-e illustrated in FIG. 6. In addition to the ICE 140, the computational branch 190-e further includes an optical transducer 160 with a combination of a multi-element detector 162 and a summing module 164.

Here, the ICE core 180 is a conventional ICE having an optical spectrum $W(\lambda)$ 150' related, over a processing wavelength range [$\lambda_{min}$, $\lambda_{max}$], to the characteristic of the sample to be measured. Structure of the ICE core 180 is described above in connection with FIG. 1C. The PWS 170' is a dispersive optical element having a discrete optical spectrum $z(\lambda)$ 152 over an operational wavelength range [$\lambda_1 \leq \lambda_{min}$, $\lambda_N \leq \lambda_{max}$]. Structure of the PWS 170' is described above in connection with FIG. 1B, where the diffractive structures 175 of the PWS 170' are arranged in accordance with the arrangement 185. In the implementation 190-e of the computational branch, the ICE core 180 is integrally formed on (e.g., directly deposited over) N output ports of the PWS 170'.

At an input end of the computational branch 190-e of an optical analysis tool, the PWS 170' receives, at an input port thereof, light modified by a sample. The sample modified light has an unknown spectrum $I(\lambda)$ 135'. The PWS 170' provides sample modified light at each of the N output ports, such that the sample modified light provided at the $j^{th}$ output port has wavelengths in an associated wavelength sub-range $\lambda_j$, where j=1 . . . N. In this manner, the sample modified light provided at the N output ports of the PWS 170' has a discrete spectrum i={$I(\lambda_j)$, j=1 . . . N} over the operational wavelength range [$\lambda_1$, $\lambda_N$], where, for each wavelength sub-range $\lambda_j$, the discrete modified spectrum i represents a respective value $I(\lambda_j)$ of the unknown spectrum $I(\lambda)$ 135' of the sample modified light. Sample modified light provided at some of the N output ports of the PWS 170' with wavelengths within the processing wavelength range [$\lambda_{min}$, $\lambda_{max}$] is processed by the ICE core 180 by weighting the discrete modified spectrum i by the optical spectrum $W(\lambda)$ 150'. The sample modified light provided at the remaining ones of the N output ports with wavelengths within the wavelength ranges [$\lambda_1$, $\lambda_{min}$] and [$\lambda_{min}$, $\lambda_{max}$] is blocked by the ICE core 180. In this manner, the ICE core 180 outputs a set of beams of processed light having a discrete processed spectrum p={$w(\lambda_j)I(\lambda_j)$, with j being in a subset of 1 . . . N for which $\lambda_{min} \leq \lambda_j \leq \lambda_{max}$} 155', where, for each wavelength sub-range $\lambda_j$, the discrete processed spectrum 155' represents a respective value $I(\lambda_j)$ of the unknown spectrum $I(\lambda)$ 135' of the sample modified light weighted by a corresponding value $w(\lambda_j)$ of the optical spectrum $W(\lambda)$ 150' associated with the characteristic to be measured.

The multi-element detector 162 of the optical transducer 160 receives the beams of processed light separated in respective wavelength sub-ranges $\lambda_j$, where j is in a subset of 1 . . . N for which $\lambda_{min} \leq \lambda_j \leq \lambda_{max}$, and outputs an intermediary detector signal including a set of voltages u={$u(\lambda_j)$, with j being in a subset of 1 . . . N for which $\lambda_{min} \leq \lambda_j \leq \lambda_{max}$} 165''' corresponding to the wavelength sub-ranges $\lambda_j$ within the processing wavelength range [$\lambda_{min}$, $\lambda_{max}$]. The set of voltages 165''' represents a mapping of the discrete processed spectrum 155' over the processing wavelength range [$\lambda_{min}$, $\lambda_{max}$] of the processed light. The summing module 164 adds the voltages $u(\lambda_j)$ corresponding to the wavelength sub-ranges $\lambda_j$, where j is in a subset of 1 . . . N for which $\lambda_{min} \leq \lambda_j \leq \lambda_{max}$, and outputs a detector signal. At an output end of the computational branch 190-*e*, a value $\Sigma w(\lambda_j)I(\lambda_j)$ 165' of a signal output by the summing module 164 is proportional to a value c' of the characteristic of the sample.

Moreover, in implementations of the optical analysis tool 110 in which the computational branch 190-*e* illustrated in FIG. 6 is used without the spectroscopic branch 192 illustrated in FIG. 2, the set of voltages u={u($\lambda_j$), with j being in a subset of 1 . . . N for which $\lambda_{min} \leq \lambda_j \leq \lambda_{max}$} 165''' of the intermediary detector signal also can be output as an additional detector signal that maps the discrete processed spectrum 155' over the processing wavelength range [$\lambda_{min}$, $\lambda_{max}$] of the processed light. In this manner, the voltages u($\lambda_j$) corresponding to the wavelength sub-ranges $\lambda_j$, where j is in a subset of 1 . . . N for which $\lambda_{min} \leq \lambda_j \leq \lambda_{max}$, can be used in combination with the known values w($\lambda_j$) of the ICE core spectrum 150 over the processing wavelength range [$\lambda_{min}$, $\lambda_{max}$] to determine the discrete spectrum i={I($\lambda_j$), with j being in a subset of 1 . . . N for which $\lambda_{min} \leq \lambda_j \leq \lambda_{max}$} 155'' of the sample modified light over the processing wavelength range [$\lambda_{min}$, $\lambda_{max}$]. As p=w*i, the processed spectrum 155' is multiplied by the inverse of the ICE core spectrum 150 to obtain the sample modified spectrum: $w^{-1}*p = w^{-1}*(w*i) = (w^{-1}*w)*i = i$. Hence, a set of voltages v={v($\lambda_1$), with j being in a subset of 1 . . . N for which $\lambda_{min} \leq \lambda_j \leq \lambda_{max}$} 165'' that maps the discrete spectrum 155'' of the sample modified light over the processing wavelength range [$\lambda_{min}$, $\lambda_{max}$] is determined as $v(\lambda_j) = w^{-1}(\lambda_j)u(\lambda_j)$, for each sub-wavelength range $\lambda_j$, where j is in a subset of 1 . . . N for which $\lambda_{min} \leq \lambda_j \leq \lambda_{max}$.

Figure 7A:
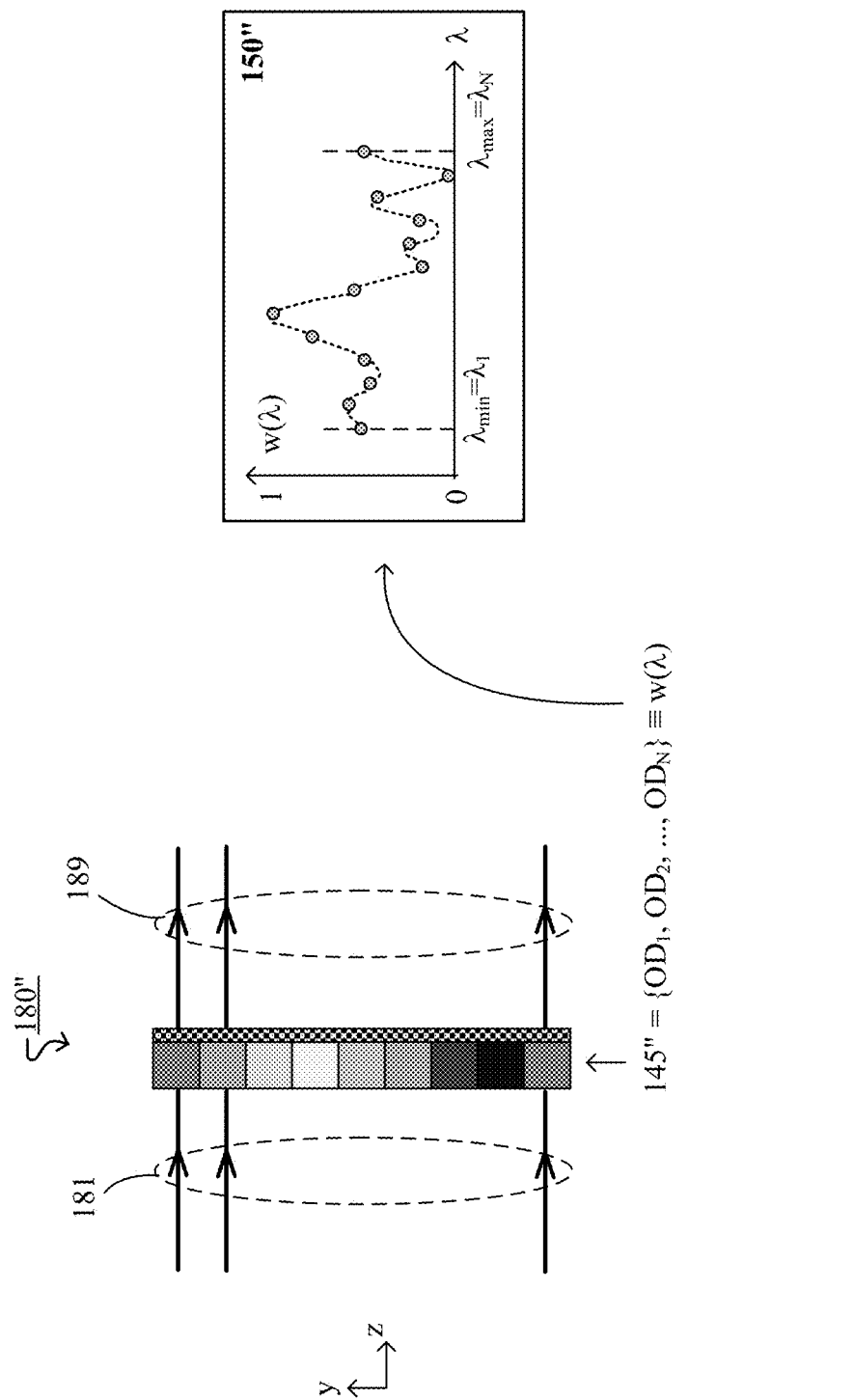

In the implementations 190-*d* and 190-*e* of the computational branch, the conventional ICE core 180 has a structure like the ones described above in connection with FIG. 1C. Another structure of another conventional ICE core 180'' that can be used in the implementations 190-*d* and 190-*e* of the computational branch is illustrated in FIG. 7A. The conventional ICE core 180'' includes a set 145'' of N neutral density filters {$OD_1$, $OD_2$, . . . , $OD_N$} laterally distributed on a substrate such that each neutral density filter $OD_j$, where j=1 . . . N, is illuminated by a respective $j^{th}$ beam of a set 181 of N beams of input light. Here, input light in the $j^{th}$ beam has wavelengths in an associated wavelength sub-range $\lambda_j$, where j=1 . . . N. Attenuation values provided by the neutral density filters of the set 145'' correspond to a discrete optical spectrum w($\lambda$) 150'' associated with this embodiment of the conventional ICE core 180'', represented in FIG. 7A by filled circles. In this manner, a discrete spectrum of a set 189 of N beams of output light represents a discrete spectrum of the set 181 of N beams of input light weighted by the discrete optical spectrum w($\lambda$) 150'' associated with the conventional ICE core 180''. In this example, a processing wavelength range [$\lambda_{min}$, $\lambda_{max}$] of the ICE core 180'' coincides with an operational wavelength range [$\lambda_1$, $\lambda_N$] of the ICE 140 with planar waveguide: [$\lambda_{min}$, $\lambda_{max}$]=[$\lambda_1$, $\lambda_N$]. In general, the processing wavelength range [$\lambda_{min}$, $\lambda_{max}$] of the ICE core 180'' is included in the operational wavelength range [$\lambda_1 \leq \lambda_{min} \leq \lambda_N \leq \lambda_{max}$] of the ICE 140 with planar waveguide. As such, neutral density filters $OD_j$ corresponding to wavelength sub-ranges $\lambda_j$ within [$\lambda_1$, $\lambda_{min}$] and [$\lambda_{max}$, $\lambda_N$] are configured to block beams of light incident thereon.

The conventional ICE core 180'' also can be used in an implementation 190-*f* of the computational branch of an optical analysis tool illustrated in FIG. 7B, as described below. The computational branch 190-*f* has an ICE 140 including a combination of the ICE core 180'' and a planar waveguide-based spectrograph (PWS) 170' for measuring a characteristic of a sample. In addition to the ICE 140, the computational branch 190-*f* further includes an optical transducer 160 with a combination of a multi-element detector 162 and a summing module 164. Here, a lateral distribution of the N neutral density filters {$OD_1$, $OD_2$, $OD_N$} of the set 145'' included in the ICE core 180'' matches a lateral distribution of N elements of the multi-element detector 162. Additionally, the N neutral density filters {$OD_1$, $OD_2$, $OD_N$} of the set 145'' are disposed on respective input surfaces of the N elements of the multi-element detector 162. Further, the PWS 170' is a dispersive optical element having a discrete optical spectrum z($\lambda$) 152 over an operational wavelength range [$\lambda_1 \leq \lambda_{min} \leq \lambda_N \leq \lambda_{max}$]. Structure of the PWS 170' is described above in connection with FIG. 1B, where the diffractive structures 175 of the PWS 170' are arranged in accordance with the arrangement 185.

The computational branch 190-*f* can be included, for example, in the optical analysis tool 110 described above in connection with FIG. 1A. As another example, the computational branch 190-*f* can be used in conjunction with the spectrographic branch 192 as described above in connection with FIG. 2, e.g., by simply replacing the computational branch 190-*a* illustrated in FIG. 2 with the computational branch 190-*f* illustrated in FIG. 7B.

At an input end of the computational branch 190-*f*, the PWS 170' receives, at an input port thereof, light modified by a sample. The sample modified light has an unknown spectrum I($\lambda$) 135'. The PWS 170' outputs a set of N beams of sample modified light at the N output ports, such that a beam of sample modified light output at the $j^{th}$ output port has wavelengths in an associated wavelength sub-range $\lambda_j$, where j=1 . . . N. In this manner, the set of N beams of sample modified light output at the N output ports of the PWS 170' has a discrete spectrum i={I($\lambda_j$), j=1 . . . N} 155'' over the operational wavelength range [$\lambda_1$, $\lambda_N$], where, for each wavelength sub-range $\lambda_j$, the discrete modified spectrum 155'' represents a respective value I($\lambda_j$) of the unknown spectrum I($\lambda$) 135' of the sample modified light. The N beams of sample modified light are directed from the N output ports of the PWS 170' to the ICE core 180'' that is integrally formed with the multi-element detector 162 of the optical transducer 160. As such, the ICE core 180'' processes some of the N beams of sample modified light—directed from output ports of the PWS 170' corresponding to the processing wavelength range [$\lambda_{min}$, $\lambda_{max}$]—a by weighting the discrete modified spectrum 155'' by the discrete optical spectrum w($\lambda$) 150'', and blocks remaining ones of the N beams of sample modified light directed from output ports of the PWS 170' corresponding to wavelength ranges [$\lambda_1$, $\lambda_{min}$] and [$\lambda_{max}$, $\lambda_N$]. In this manner, the ICE core 180'' provides, to some of the N elements of the multi-element detector 162, spatially separated processed light having a discrete processed spectrum p={w($\lambda_j$)I($\lambda_j$), with j being in a subset of 1 . . . N for which $\lambda_{min} \leq \lambda_j \leq \lambda_{max}$}, where, for each wavelength sub-range $\lambda_j$, the discrete processed spectrum 155' represents a respective value I($\lambda_j$) of the unknown spectrum I($\lambda$) 135' of the sample modified light weighted by a corresponding value w($\lambda_j$) of the discrete optical spectrum w($\lambda$) 150'' associated with the characteristic to be measured.

The multi-element detector 162 outputs an intermediary detector signal including a set of voltages u={u($\lambda_j$), with j being in a subset of 1 . . . N for which $\lambda_{min} \leq \lambda_j \leq \lambda_{max}$} 165'' corresponding to the wavelength sub-ranges $\lambda_j$ within the processing wavelength range [$\lambda_{min}$, $\lambda_{max}$]. The set of voltages 165''' represents a mapping of the discrete processed spectrum p over the processing wavelength range [$\lambda_{min}$, $\lambda_{max}$] of the processed light. The summing module 164 adds the voltages $u(\lambda_j)$ corresponding to the wavelength sub-ranges $\lambda_j$, where j is in a subset of 1 . . . N for which $\lambda_{min} \leq \lambda_j \leq \lambda_{max}$, and outputs a detector signal. At an output end of the computational branch 190-f, a value $\Sigma w(\lambda_j)I(\lambda_j)$ 165' of a signal output by the summing module 164 is proportional to a value c' of the characteristic of the sample.

Figure 7B:
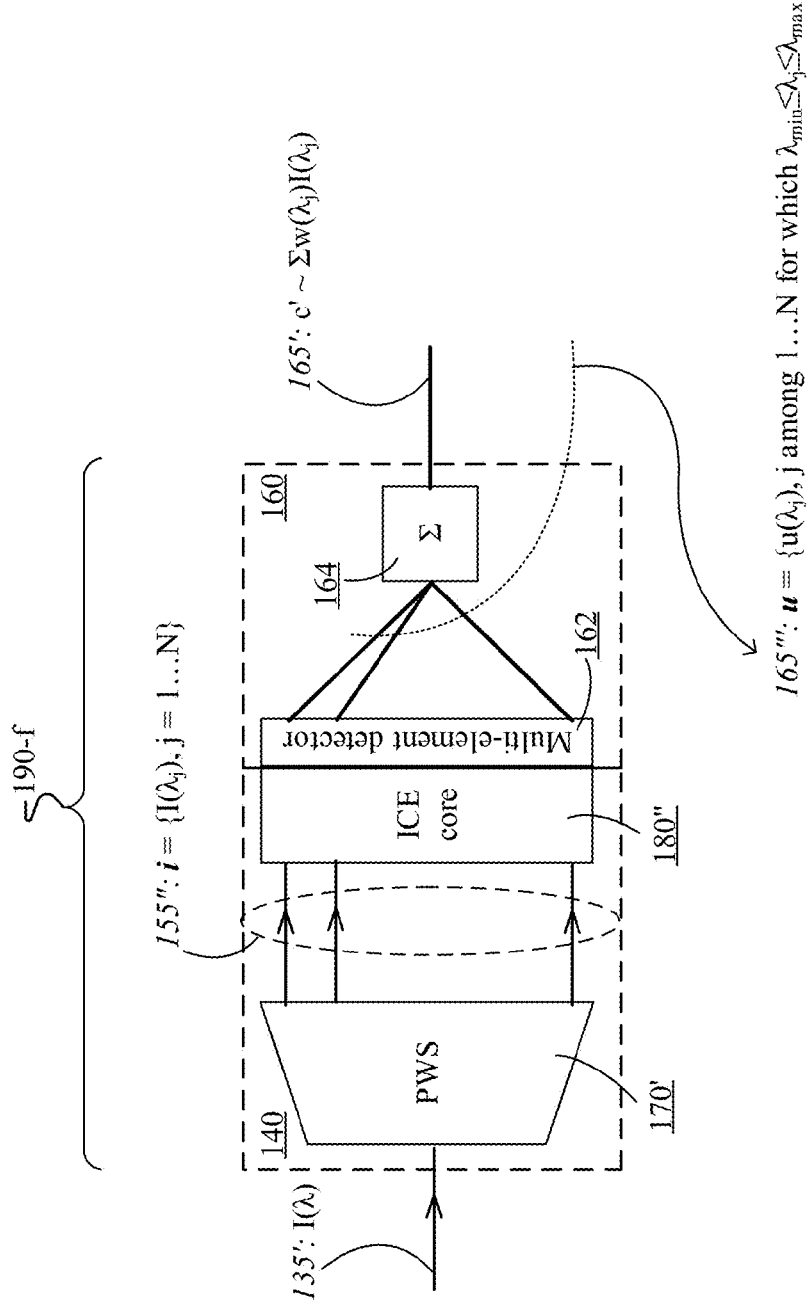

Moreover, in implementations of the optical analysis tool 110 in which the computational branch 190-f illustrated in FIG. 7B is used without the spectroscopic branch 192 illustrated in FIG. 2, the set of voltages $u=\{u(\lambda_j)$, with j being in a subset of 1 . . . N for which $\lambda_{min} \leq \lambda_j \leq \lambda_{max}\}$ 165''' of the intermediary detector signal also can be output as an additional detector signal that maps the discrete processed spectrum p over the processing wavelength range [$\lambda_{min}$, $\lambda_{max}$] of the processed light. In this manner, the voltages $u(\lambda_j)$ corresponding to the wavelength sub-ranges $\lambda_j$, where j is in a subset of 1 . . . N for which $\lambda_{min} \leq \lambda_j \leq \lambda_{max}$, can be used in combination with the known values $w(\lambda_j)$ of the ICE core spectrum 150 over the processing wavelength range [$\lambda_{min}$, $\lambda_{max}$] to determine the discrete spectrum $i=\{I(\lambda_j)$, with j being in a subset of 1 . . . N for which $\lambda_{min} \leq \lambda_j \leq \lambda_{max}\}$ 155" of the sample modified light over the processing wavelength range [$\lambda_{min}$, $\lambda_{max}$]. As p=w*i, the processed spectrum p is multiplied by the inverse of the ICE core spectrum 150 to obtain the sample modified spectrum: $w^{-1}*p=w^{-1}*(w*i)=(w^{-1}*w)*i=i$. Hence, a set of voltages $v=\{v(\lambda_j)$, with j being in a subset of 1 . . . N for which $\lambda_{min} \leq \lambda_j \leq \lambda_{max}\}$ 165" that maps the discrete spectrum 155" of the sample modified light over the processing wavelength range [$\lambda_{min}$, $\lambda_{max}$] is determined as $v(\lambda_j)=w^{-1}(\lambda_j)u(\lambda_j)$, for each sub-wavelength range $\lambda_j$, where j is in a subset of 1 . . . N for which $\lambda_{min} \leq \lambda_j \leq \lambda_{max}$.

Multiple implementations 190-b, 190-c, 190-d, 190-e and 190-f of the computational branch of an optical analysis tool were described above, each of which including a combination of a conventional ICE core (180 or 180") and a PWS 170'. Other implementations of the computational branch of an optical analysis tool are described below in which a single optical device including a planar waveguide provides functionalities previously provided, as disclosed above, by a combination of a conventional ICE core and PWS.

Figure 8:
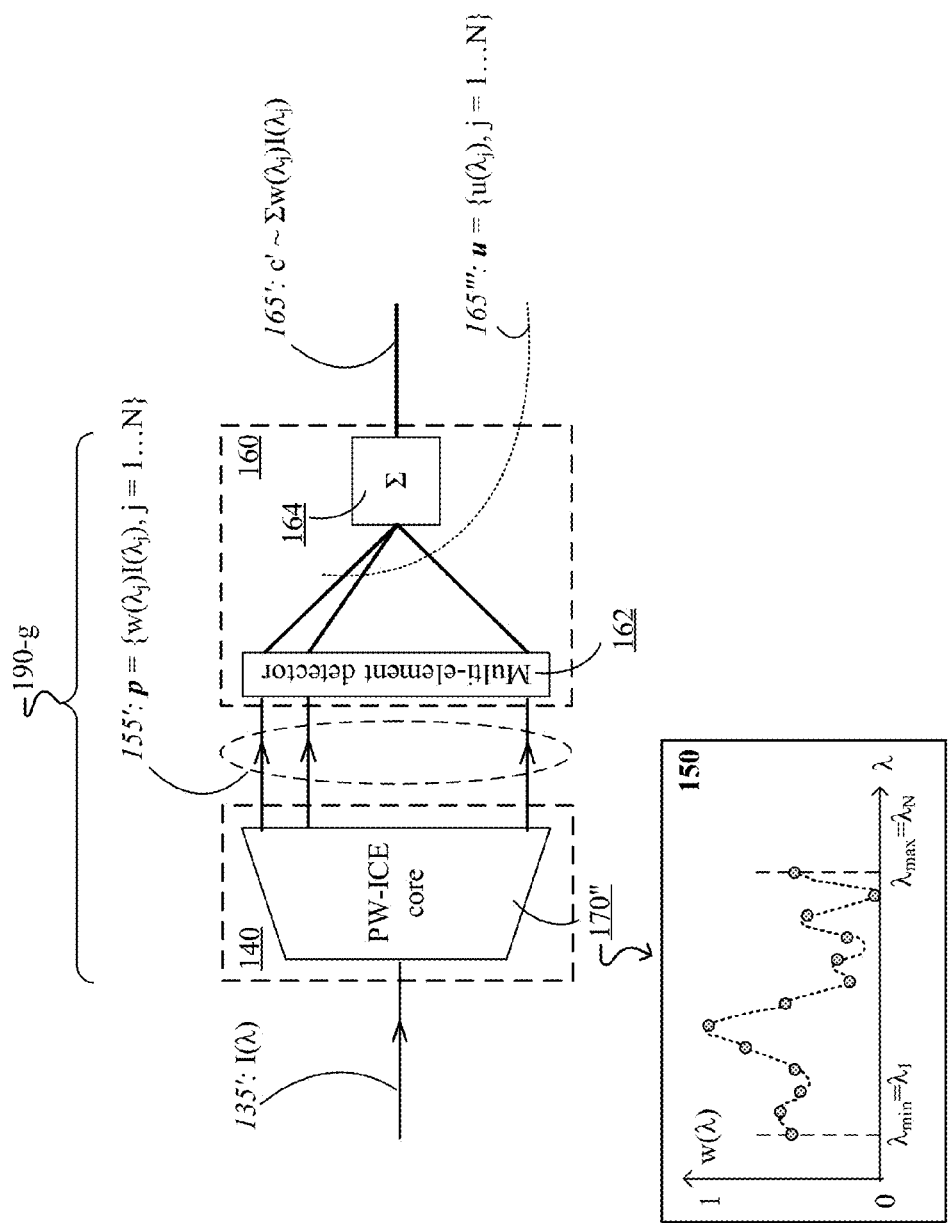
FIG. 8 shows a portion of an embodiment of an optical analysis tool with an ICE including a planar waveguide-based ICE core for measuring a characteristic of a sample.

FIG. 8 shows a computational branch 190-g of an optical analysis tool with an ICE 140 including a planar waveguide-based ICE core 170" for measuring a characteristic of a sample. For example, the computational branch 190-g can be included in the optical analysis tool 110 described above in connection with FIG. 1A. As another example, the computational branch 190-g can be used in conjunction with the spectrographic branch 192 as described above in connection with FIG. 2, e.g., by simply replacing the computational branch 190-a illustrated in FIG. 2 with the computational branch 190-g illustrated in FIG. 8. In addition to the ICE 140, the computational branch 190-g further includes an optical transducer 160 with a combination of a multi-element detector 162 and a summing module 164.

Here, the PW-ICE core 170" is the dispersive optical element described above in connection with FIG. 1B, where the diffractive structures 175 of the PW-ICE core 170" are arranged in accordance with the arrangement 145. In this manner, the PW-ICE core 170" has a discrete optical spectrum $w(\lambda)$ 150 related, over a processing wavelength range [$\lambda_{min}$, $\lambda_{max}$], to the characteristic of the sample to be measured. As $\lambda_{min}=\lambda_1$ and $\lambda_{max}=\lambda_N$, an operational wavelength range of the ICE 140 coincides with the processing wavelength range [$\lambda_{min}$, $\lambda_{max}$] of the PW-ICE core 170".

At an input end of the computational branch 190-g of an optical analysis tool, the PW-ICE core 170" receives, at an input port thereof, light modified by a sample. The sample modified light has an unknown spectrum $I(\lambda)$ 135'. The PW-ICE core 170" processes the sample modified light by weighting the unknown spectrum $I(\lambda)$ 135' by the discrete optical spectrum $w(\lambda)$ 150 over the processing wavelength range [$\lambda_{min}$, $\lambda_{max}$]. Moreover, the PW-ICE core 170" outputs N beams of processed light at respective N output ports of the PW-ICE core 170", such that the processed light provided at the $j^{th}$ output port has wavelengths in an associated wavelength sub-range $\lambda_j$, where j=1 . . . N. In this manner, a set of the N beams of processed light output at the N output ports of the PW-ICE core 170" has a discrete processed spectrum $p=\{w(\lambda_j)I(\lambda_j)$, j=1 . . . N\} 155' over the processing wavelength range [$\lambda_{min}$, $\lambda_{max}$], where, for each wavelength sub-range $\lambda_j$, the discrete processed spectrum 155' represents a respective value $I(\lambda_j)$ of the unknown spectrum $I(\lambda)$ 135' of the sample modified light weighted by a corresponding value $w(\lambda_j)$ of the discrete optical spectrum $w(\lambda)$ 150 associated with the characteristic to be measured.

The multi-element detector 162 of the optical transducer 160 receives the N beams of processed light separated in respective wavelength sub-ranges $\{\lambda_j$, j=1 . . . N\} and outputs an intermediary detector signal including a set of voltages $u=\{u(\lambda_j)$, j=1 . . . N\} 165''' corresponding to the respective wavelength sub-ranges $\{\lambda_j$, j=1 . . . N\}. The set of voltages 165''' represents a mapping of the discrete processed spectrum 155' over the processing wavelength range [$\lambda_{min}$, $\lambda_{max}$] of the processed light. The summing module 164 adds the voltages $u(\lambda_j)$ corresponding to the respective wavelength sub-ranges $\{\lambda_j$, j=1 . . . N\} from the set 165''' and outputs a detector signal. At an output end of the computational branch 190-g, a value $\Sigma w(\lambda_j)I(\lambda_j)$ 165' of a signal output by the summing module 164 is proportional to a value c' of the characteristic of the sample.

Moreover, in implementations of the optical analysis tool 110 in which the computational branch 190-g illustrated in FIG. 8 is used without the spectroscopic branch 192 illustrated in FIG. 2, the set of voltages $u=\{u(\lambda_j)$, j=1 . . . N\} 165''' of the intermediary detector signal also can be output as an additional detector signal that maps the discrete processed spectrum 155' over the processing wavelength range [$\lambda_{min}$, $\lambda_{max}$] of the processed light. In this manner, the voltages $u(\lambda_j)$ corresponding to the wavelength sub-ranges $\{\lambda_j$, j=1 . . . N\} can be used in combination with the known values $w(\lambda_j)$ of the ICE core spectrum 150 over the processing wavelength range [$\lambda_{min}$, $\lambda_{max}$] to determine the discrete spectrum $i=\{I(\lambda_j)$, j=1 . . . N\} 155" of the sample modified light over the processing wavelength range [$\lambda_{min}$, $\lambda_{max}$]. As p=w*i, the processed spectrum 155' is multiplied by the inverse of the ICE core spectrum 150 to obtain the sample modified spectrum: $w^{-1}*p=w^{-1}*(w*i)=(w^{-1}*w)*i=i$. Hence, a set of voltages $v=\{v(\lambda_j)$, j=1 . . . N\} 165" that maps the discrete spectrum 155" of the sample modified light over the processing wavelength range [$\lambda_{min}$, $\lambda_{max}$] is determined as $v(\lambda_j)=w^{-1}(\lambda_j)u(\lambda_j)$, for each sub-wavelength range $\lambda_j$, where j=1 . . . N.

Figure 9C:
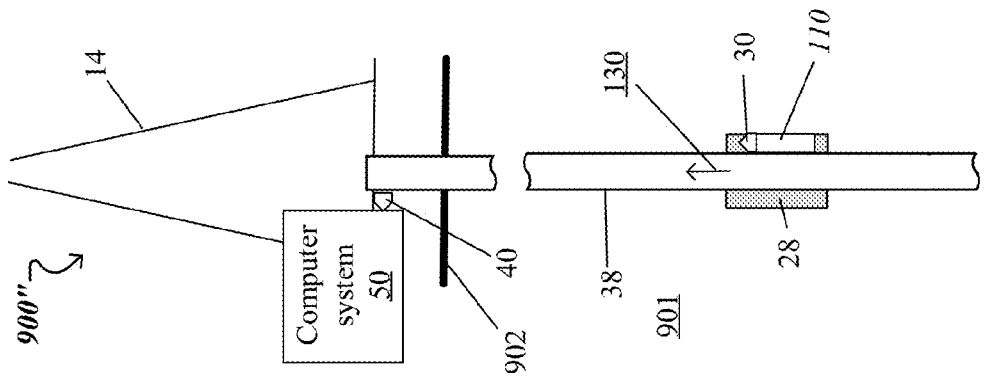
FIGS. 9A-9C show multiple configurations of an example of a system for analyzing wellbore fluids that uses a well logging tool including an ICE with a planar waveguide.
Figure 9B:
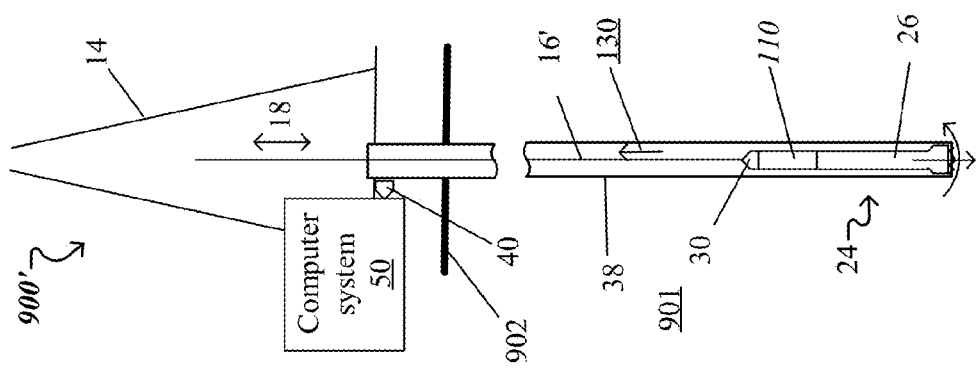
Figure 9A:
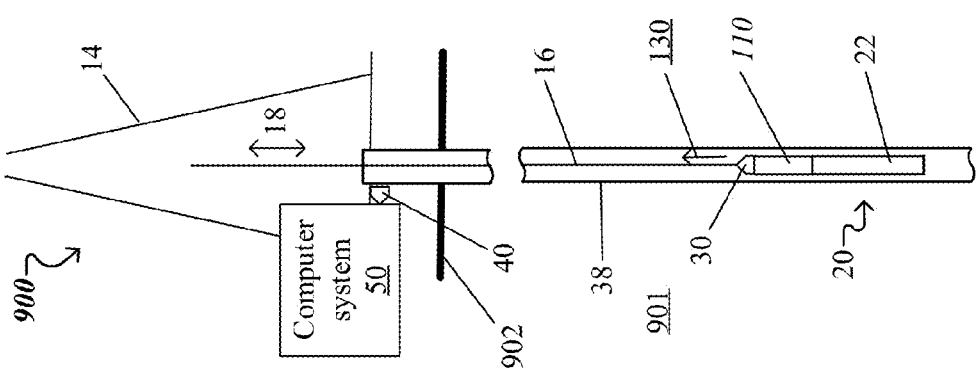

FIGS. 9A-9C show multiple configurations 900, 900', 900" of an example of a system for analyzing wellbore fluids 130, such that analyses are generated from at least some measurements taken with an optical analysis tool 110, which includes an ICE with a planar waveguide, such as the one described above in connection with FIG. 1A. Here, the optical analysis tool 110 is referred to as a well logging tool 110, and the disclosed system is referred to as a well logging system.

Each of the configurations 900, 900', 900" of the well logging system illustrated in FIGS. 9A-9C includes a rig 14 above the ground surface 902 and a wellbore 38 below the ground surface. The wellbore 38 extends from the ground surface into the earth 901 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 902, for instance. Additionally, surface applications of the well logging tool 110 may include water monitoring and gas and crude transportation and processing.

FIG. 9A shows a configuration 900 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 900 of the well logging system, this information can be generated as a function of a distance (e.g., a depth) with respect to the ground surface 902. In the example illustrated in FIG. 9A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics (and, optionally, records optical spectra of wellbore fluid modified light acquired when the values of the one or more characteristics were determined) in real time and reports those values (and, optionally, the recorded optical spectra) instantaneously as they occur in the flowing stream of wellbore fluids 130, sequentially to or simultaneously with other measurement/logging tools 22 of the tool string 20.

FIG. 9B shows another configuration 900' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 902, where the returned drilling mud can be resupplied to the drill string 16' (not shown in FIG. 9B). In this case, the MWD/LWD-configured well logging tool 110 generates and logs information about the wellbore fluids 130 (e.g., drilling mud in this case) adjacent the working drill bit 26.

FIG. 9C shows yet another configuration 900" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of (and, optionally, spectra of light modified by) the wellbore fluids 130 adjacent the underground location of the casing collar 28.

In each of the above configurations 900, 900' and 900" of the well logging system, the values of the one or more characteristics measured by the well logging tool 110 (and, optionally, optical spectra of wellbore fluid modified light acquired by the well logging tool 110 when the values of the one or more characteristics were measured) are provided (e.g., as a detector signal 165 including a scalar component 165' proportional to a value of a characteristic to be measured, and, optionally, a vector component 165" that represents an optical spectrum of wellbore fluid modified light acquired when the value of the characteristic was measured) to the telemetry transmitter 30. The latter communicates the measured values (and acquired optical spectrum) to a telemetry receiver 40 located above the ground surface 902. The telemetry transmitter 30 and the telemetry receiver 40 can communicate through a wired or wireless telemetry channel. In some implementations of the system configurations 900, 900' illustrated in FIGS. 9A and 9B, e.g., in slickline or coiled tubing applications, measurement data (e.g., characteristic values and concurrently acquired optical spectrum) generated by the well logging tool 110 can be written locally to memory of the well logging tool 110.

The measured values of the one or more characteristics of the wellbore fluids 130 (and, optionally, a spectrum of wellbore fluid modified light acquired when the characteristics were measured) received by the telemetry receiver 40 can be logged and analyzed by a computer system 50 associated with the rig 14. In this manner, the characteristic measurement values (and, optionally, the spectrum of wellbore fluid modified light acquired when the characteristics were measured) provided by the well logging tool 110 can be used to generate physical and chemical information about the wellbore fluids 130 in the wellbore 38.

Characteristics of the wellbore fluids 130 that can be related to the modified spectrum 135' through the optical spectra associated with any of the ICE cores of the ICE 140 with planar waveguide described herein are: concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

In general, innovative aspects of the technologies described herein can be implemented in optical analysis tools that include one or more of the following aspects:

In general aspect 1, an optical analysis tool comprises: an integrated computational element (ICE) to receive, when the tool is operated, light from a sample, and process at least a portion of the received light, such that the processed light is related, over a processing wavelength range, to a characteristic of the sample. In the general aspect 1, the ICE comprises a dispersive optical element comprising an input port; a substrate and a planar waveguide disposed on the substrate, the planar waveguide to guide light input through the input port, such that the guided light is within an operational wavelength range that encompasses the processing wavelength range; diffractive structures distributed along the planar waveguide to spatially separate the guided light into a plurality of wavelength sub-ranges of the operational wavelength range; and a plurality of output ports to output the spatially separated light of the respective wavelength sub-ranges.

Aspect 2 according to aspect 1, wherein a distribution of the diffractive structures is such that the dispersive optical element functions as a spectrograph that weights the respective wavelength sub-ranges of the spatially separated light by substantially equal amounts, and the ICE further comprises an ICE core that weights light incident thereof by differing amounts corresponding to the wavelength sub-ranges within the processing wavelength range, the different amounts being related to the characteristic of the sample.

Aspect 3 according to aspect 2, wherein the ICE core is optically coupled to the input port of the spectrograph, such that the light input to the input port is sample modified light weighted by the ICE core, and the light output at some of the output ports of the spectrograph (i) is the weighted light spatially separated into the respective wavelength sub-ranges within the processing wavelength range and (ii) represents the light processed by the ICE. In aspect 3, the optical analysis tool further comprises a multi-element detector to receive the processed light from the output ports of the spectrograph, and provide a multi-element detector signal corresponding to a spectrum of the processed light; and a summing module to integrate the multi-element detector signal, and provide an output signal corresponding to a value of the characteristic of the sample.

Aspect 4 according to aspect 3, wherein the ICE further comprises a second ICE core to weight light incident thereof by other differing amounts corresponding to the wavelength sub-ranges within a second processing wavelength range, the other different amounts being related to a second characteristic of the sample; and a switch to toggle between a first state of the ICE in which the ICE core is coupled to and the second ICE core is decoupled from the input port of the spectrograph, and a second state of the ICE in which the second ICE core is coupled to and the ICE core is decoupled from the input port of the spectrograph.

Aspect 5 according to aspects 3 or 4, wherein the ICE further comprises a switch to toggle between a first state of the ICE in which the ICE core is coupled to the input port of the spectrograph, and a second state of the ICE in which the ICE core is decoupled from the input port of the spectrograph and the sample modified light is input directly to the input port.

Aspect 6 according to aspect 2 or aspect 3, wherein the ICE core is disposed on an input facet of the spectrograph that includes the input port.

Aspect 7 according to aspect 2, wherein the light input to the input port is sample modified light; the light output at the output ports of the spectrograph is the sample modified light spatially separated into the respective wavelength sub-ranges of the operational wavelength range; the ICE core is optically coupled to the output ports of the spectrograph, such that the ICE (i) weights the light within the processing wavelength range from the output ports and (ii) provides the weighted light as the light processed by the ICE. In aspect 7, the optical analysis tool further comprises a multi-element detector to receive the processed light from the ICE core, and provide a multi-element detector signal corresponding to a spectrum of the processed light; and a summing module to integrate the multi-element detector signal, and provide an output signal corresponding to a value of the characteristic of the sample.

Aspect 8 according to aspect 7, wherein the ICE further comprises a second ICE core to weight light incident thereof by other differing amounts corresponding to the wavelength sub-ranges within a second processing wavelength range, the other different amounts being related to a second characteristic of the sample; and a switch to toggle between a first state of the ICE in which the ICE core is coupled to and the second ICE core is decoupled from the output ports of the spectrograph, and a second state of the ICE in which the second ICE core is coupled to and the ICE core is decoupled from the output ports of the spectrograph.

Aspect 9 according to aspect 7, wherein the ICE further comprises a switch to toggle between a first state of the ICE in which the ICE core is coupled to the output ports of the spectrograph, and a second state of the ICE in which the ICE core is decoupled from the output ports of the spectrograph and the light from the output ports is output directly to the multi-element detector.

Aspect 10 according to aspects 5 or 9, wherein when the ICE is in the second state the spectrograph receives at the input port sample modified light and outputs at the output ports the sample modified light spatially separated into the respective wavelength sub-ranges within the operational wavelength range, and the multi-element detector receives from the output ports of the spectrograph the spatially-separated sample modified light, and provides a multi-element detector signal corresponding to a spectrum of the sample modified light. In aspect 10, the optical analysis tool further comprises a non-transitory storage medium to store the multi-element detector signal corresponding to the spectrum of the sample modified light.

Aspect 11 according to aspect 2 or aspect 7, wherein the ICE core is disposed on an output facet of the spectrograph that includes the output ports.

Aspect 12 according to aspect 2 or aspect 7, wherein the ICE core is disposed on an input surface of the multi-element detector.

Aspect 13 according to aspect 12, wherein the ICE core comprises a plurality of neutral density filters corresponding to the wavelength sub-ranges within the processing wavelength range; and a lateral distribution of the neutral density filters corresponds to a lateral distribution of elements of the multi-element detector.

Aspect 14 according to aspect 2 or any one of aspects 7 to 13, wherein the light input to the input port of the spectrograph is a portion of sample modified light. In aspect 14, the optical analysis tool further comprises a multi-element detector to receive the spatially separated light from the output ports of the spectrograph, and provide a multi-element detector signal corresponding to a spectrum of the sample modified light; and an optical transducer to integrate the remaining portion of sample light processed by the ICE, and provide an optical transducer signal corresponding to a value of the characteristic of the sample.

Aspect 15 according to aspect 14, further comprising non-transitory storage medium to store the multi-element detector signal corresponding to a spectrum of the sample modified light.

Aspect 16 according to aspect 14, further comprising non-transitory storage medium; and a comparator module to determine whether the provided value of the characteristic of the sample is valid, and if not so, record onto the non-transitory storage medium the provided multi-element detector signal corresponding to the spectrum of the sample modified light.

Aspect 17 according to aspect 16, wherein, to be valid, the provided value of the characteristic of the sample is within a predetermined value range.

Aspect 18 according to aspect 15 or aspect 16, wherein either the non-transitory storage medium or the comparator module or both are located remotely from a portion of the optical analysis tool that includes the ICE core and the spectrograph.

Aspect 19 according to aspect 1, wherein a distribution of the diffractive structures is such that the dispersive optical element functions as an ICE core that weights the respective wavelength sub-ranges of the spatially separated light by differing amounts corresponding to the wavelength sub-ranges, the differing amounts being related to the characteristic of the sample.

Aspect 20 according to aspect 19, wherein the light input to the input port is sample modified light; the processing wavelength range is the operational wavelength range; and the light output at the output ports of the spectrograph is (i) the weighted sample modified light spatially separated into the respective wavelength sub-ranges of the operational wavelength range and (ii) represents the light processed by the ICE. In aspect 20, the optical analysis tool further comprises a multi-element detector to receive the processed light from the output ports of the ICE core, and provide a multi-element detector signal corresponding to a spectrum of the processed light; and a summing module to integrate the multi-element detector signal, and provide an output signal corresponding to a value of the characteristic of the sample.

Aspect 21 according to any one of aspects 3 to 11 and 14 to 18, wherein the ICE core comprises a substrate having a first surface, wherein the substrate comprises a substrate material with a substrate material refractive index; and a plurality of layers stacked on the first surface of the substrate, wherein adjacent ones of the plurality of layers respectively comprise layer materials with refractive indices different from each other, wherein a substrate thickness and thicknesses of the plurality of layers are such that the light weighted by the ICE core is related, over the processing wavelength range, to the characteristic of the sample.

Aspect 22 according to any one of aspects 3 to 13 or 20, further comprising a non-transitory storage medium to store the multi-element detector signal corresponding to the spectrum of the processed light.

Aspect 23 according to any one of aspects 3 to 13 or 20, further comprising a hardware processor to determine a spectrum of the sample modified light based on (i) the multi-element detector signal corresponding to the spectrum of the processed light, and (ii) an optical spectrum associated with the ICE core; and a non-transitory storage medium to store the determined spectrum of the sample modified light.

Aspect 24 according to any preceding aspect, further comprising a light source positioned to illuminate the sample, such that the light received by the ICE from the sample constitutes sample modified light, wherein a spectrum of light corresponding to the light source overlaps with the processing wavelength range.

Aspect 25 according to any preceding aspect, wherein the processing wavelength range comprises wavelengths in a range from about 0.2 µm to about 2.5 µm.

Aspect 26 according to any preceding aspect, wherein a refractive index of the planar waveguide's material is larger than a refractive index of the substrate's material. In aspect 26, the diffractive structures of the dispersive optical element comprise a first plurality of refractive index altering features extending along a first direction in a plane of the planar waveguide, and a second plurality of refractive index altering features extending along a second direction in the plane, where the second direction is different from the first direction.

Aspect 27 according to aspect 26, wherein a width of the refractive index altering features of the first and second pluralities is selected to cause back scattering of light in respective first and second wavelength sub-ranges.

In general aspect 28, a well logging system comprises the optical analysis tool in accordance with any preceding aspect, wherein the sample comprises wellbore fluids and the characteristic of the sample is a characteristic of the wellbore fluids.

Aspect 29 according to aspect 28, wherein the characteristic of the sample is selected from the group consisting of a concentration of a substance in the sample, a pH of the sample, a ratio of concentrations of two different substances in the sample, a phase of the sample, a density of the sample, and a viscosity of the sample.

In general aspect 30, a method comprises placing the optical analysis tool in accordance with any one of aspects 1 to 27 in a wellbore; and determining the value of a characteristic of a sample in the wellbore using the optical analysis tool.

Aspect 31 according to aspect 30, further comprising collecting, while the optical analysis tool is in the wellbore, an in-situ optical spectrum of sample modified light related to the value of the characteristic.

Aspect 32 according to aspect 31, wherein said collecting the in-situ optical spectrum of the sample modified light is performed in response to determining that the value of the characteristic is outside a predetermined range of values for the characteristic. In aspect 32, the method further comprises processing a combination of the value of the characteristic and the in-situ optical spectrum to improve performance of the optical analysis tool.

Aspect 33 according to aspect 31 or aspect 32, wherein, in response to determining that the in-situ optical spectrum is not contained in an optical spectra database, the method further comprises flagging the value of the characteristic; and processing a combination of the flagged value of the characteristic and the in-situ optical spectrum to improve the performance of the optical analysis tool.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:
1. An optical analysis tool comprising:
an integrated computational element (ICE) to
receive, when the tool is operated, light from a sample, and process at least a portion of the received light, such that the processed light is related, over a processing wavelength range, comprising wavelengths in a range from about 0.2 µm to about 2.5 µm, to a characteristic of the sample,
wherein the ICE comprises
(I) a dispersive optical element comprising
an input port,
a substrate and a planar waveguide disposed on the substrate, the planar waveguide to guide light input through the input port, such that the guided light is within an operational wavelength range, comprising wavelengths in a range from about 0.2 µm to about 2.5 µm, that encompasses the processing wavelength range,
diffractive structures distributed along the planar waveguide to spatially separate the guided light into a plurality of wavelength sub-ranges of the operational wavelength range, wherein a distribution of the diffractive structures is such that the dispersive optical element functions as a spectrograph that weights the respective wavelength sub-ranges of the spatially separated light by substantially equal amounts, and
a plurality of output ports to output the spatially separated light of the respective wavelength sub-ranges; and
(II) an ICE core that weights light incident thereof by differing amounts corresponding to the wavelength sub-ranges within the processing wavelength range, the different amounts being related to the characteristic of the sample, and wherein
the diffractive structures comprise lines or grooves etched at an interface between the planar waveguide and an air environment.

2. The optical analysis tool of claim 1, wherein
the ICE core is optically coupled to the input port of the spectrograph, such that
the light input to the input port is sample modified light weighted by the ICE core, and
the light output at some of the output ports of the spectrograph (i) is the weighted light spatially separated into the respective wavelength sub-ranges within the processing wavelength range and (ii) represents the light processed by the ICE, and
the optical analysis tool further comprises
a multi-element detector to
receive the processed light from the output ports of the spectrograph, and
provide a multi-element detector signal corresponding to a spectrum of the processed light, and
a summing module to
integrate the multi-element detector signal, and
provide an output signal corresponding to a value of the characteristic of the sample.

3. The optical analysis tool of claim 2, wherein the ICE further comprises
a second ICE core to weight light incident thereof by other differing amounts corresponding to the wavelength sub-ranges within a second processing wavelength range, the other different amounts being related to a second characteristic of the sample, and
a switch to toggle between
a first state of the ICE in which the ICE core is coupled to and the second ICE core is decoupled from the input port of the spectrograph, and
a second state of the ICE in which the second ICE core is coupled to and the ICE core is decoupled from the input port of the spectrograph.

4. The optical analysis tool of claim 2, wherein the ICE further comprises
a switch to toggle between
a first state of the ICE in which the ICE core is coupled to the input port of the spectrograph, and
a second state of the ICE in which the ICE core is decoupled from the input port of the spectrograph and the sample modified light is input directly to the input port, and
when the ICE is in the second state
the spectrograph receives at the input port sample modified light and outputs at the output ports the sample modified light spatially separated into the respective wavelength sub-ranges within the operational wavelength range, and
the multi-element detector receives from the output ports of the spectrograph the spatially-separated sample modified light, and provides a multi-element detector signal corresponding to a spectrum of the sample modified light, and
the optical analysis tool further comprises a non-transitory storage medium to store the multi-element detector signal corresponding to the spectrum of the sample modified light.

5. The optical analysis tool of claim 2, further comprising
a hardware processor to determine a spectrum of the sample modified light based on (i) the multi-element detector signal corresponding to the spectrum of the processed light, and (ii) an optical spectrum associated with the ICE core; and
a non-transitory storage medium to store the determined spectrum of the sample modified light.

6. The optical analysis tool of claim 1, wherein the ICE core is disposed on an input facet of the spectrograph that includes the input port.

7. The optical analysis tool of claim 1, wherein
the light input to the input port is sample modified light,
the light output at the output ports of the spectrograph is the sample modified light spatially separated into the respective wavelength sub-ranges of the operational wavelength range,
the ICE core is optically coupled to the output ports of the spectrograph, such that the ICE (i) weights the light within the processing wavelength range from the output ports and (ii) provides the weighted light as the light processed by the ICE, and
the optical analysis tool further comprises
a multi-element detector to
receive the processed light from the ICE core, and
provide a multi-element detector signal corresponding to a spectrum of the processed light, and
a summing module to
integrate the multi-element detector signal, and
provide an output signal corresponding to a value of the characteristic of the sample.

8. The optical analysis tool of claim 7, wherein the ICE further comprises
a second ICE core to weight light incident thereof by other differing amounts corresponding to the wavelength sub-ranges within a second processing wavelength range, the other different amounts being related to a second characteristic of the sample, and
(a) a switch to toggle between
a first state of the ICE in which the ICE core is coupled to and the second ICE core is decoupled from the output ports of the spectrograph, and a second state of the ICE in which the second ICE core is coupled to and the ICE core is decoupled from the output ports of the spectrograph; or (b) a switch to toggle between
   a first state of the ICE in which the ICE core is coupled to the output ports of the spectrograph, and
   a second state of the ICE in which the ICE core is decoupled from the output ports of the spectrograph and the light from the output ports is output directly to the multi-element detector.

9. The optical analysis tool of claim 7, wherein the ICE further comprises
   a switch to toggle between
      a first state of the ICE in which the ICE core is coupled to the output ports of the spectrograph, and
      a second state of the ICE in which the ICE core is decoupled from the output ports of the spectrograph and the light from the output ports is output directly to the multi-element detector, and
   when the ICE is in the second state
      the spectrograph receives at the input port sample modified light and outputs at the output ports the sample modified light spatially separated into the respective wavelength sub-ranges within the operational wavelength range, and
      the multi-element detector receives from the output ports of the spectrograph the spatially-separated sample modified light, and provides a multi-element detector signal corresponding to a spectrum of the sample modified light, and
the optical analysis tool further comprises a non-transitory storage medium to store the multi-element detector signal corresponding to the spectrum of the sample modified light.

10. The optical analysis tool of claim 7, wherein
   the ICE core is disposed on an input surface of the multi-element detector and comprises a plurality of neutral density filters corresponding to the wavelength sub-ranges within the processing wavelength range, and
   a lateral distribution of the neutral density filters corresponds to a lateral distribution of elements of the multi-element detector.

11. The optical analysis tool of claim 1, wherein the ICE core is disposed on an output facet of the spectrograph that includes the output ports.

12. The optical analysis tool of claim 1, wherein
   the light input to the input port of the spectrograph is a portion of sample modified light, and
   the optical analysis tool further comprises
      a multi-element detector to
         receive the spatially separated light from the output ports of the spectrograph, and
         provide a multi-element detector signal corresponding to a spectrum of the sample modified light, and
      an optical transducer to
         integrate the remaining portion of sample light processed by the ICE, and
         provide an optical transducer signal corresponding to a value of the characteristic of the sample.

13. The optical analysis tool of claim 12, further comprising
   non-transitory storage medium to store the multi-element detector signal corresponding to a spectrum of the sample modified light, and
   a comparator module to
   determine whether the provided value of the characteristic of the sample is valid, and if not so,
   record onto the non-transitory storage medium the provided multi-element detector signal corresponding to the spectrum of the sample modified light,
      wherein, to be valid, the provided value of the characteristic of the sample is within a predetermined value range, and
      wherein either the non-transitory storage medium or the comparator module or both are located remotely from a portion of the optical analysis tool that includes the ICE core and the spectrograph.

14. The optical analysis tool of claim 1, further comprising:
   a light source positioned to illuminate the sample, such that the light received by the ICE from the sample constitutes sample modified light,
   wherein a spectrum of light corresponding to the light source overlaps with the processing wavelength range.

15. The optical analysis tool of claim 1, wherein
   the sample comprises wellbore fluids and the characteristic of the sample is a characteristic of the wellbore fluids, and
   the characteristic of the sample is selected from the group consisting of a concentration of a substance in the sample, a pH of the sample, a ratio of concentrations of two different substances in the sample, a phase of the sample, a density of the sample, and a viscosity of the sample.

16. An optical analysis tool comprising:
   an integrated computational element (ICE) to
      receive, when the tool is operated, light from a sample, and
      process at least a portion of the received light, such that the processed light is related, over a processing wavelength range, comprising wavelengths in a range from about 0.2 µm to about 2.5 µm, to a characteristic of the sample,
   wherein the ICE comprises
      a dispersive optical element comprising
         an input port,
         a substrate and a planar waveguide disposed on the substrate, the planar waveguide to guide light input through the input port, such that the guided light is within an operational wavelength range, comprising wavelengths in a range from about 0.2 µm to about 2.5 µm, that encompasses the processing wavelength range,
         diffractive structures distributed along the planar waveguide to spatially separate the guided light into a plurality of wavelength sub-ranges of the operational wavelength range, wherein a distribution of the diffractive structures is such that the dispersive optical element functions as an ICE core that weights the respective wavelength sub-ranges of the spatially separated light by differing amounts corresponding to the wavelength sub-ranges, the differing amounts being related to the characteristic of the sample, and
         a plurality of output ports to output the spatially separated light of the respective wavelength sub-ranges, wherein
            the diffractive structures comprise lines or grooves etched at an interface between the planar waveguide and an air environment.

17. The optical analysis tool of claim 16, wherein
   the light input to the input port is sample modified light,
   the processing wavelength range is the operational wavelength range, the light output at the output ports is (i) the weighted sample modified light spatially separated into the respective wavelength sub-ranges of the operational wavelength range and (ii) represents the light processed by the ICE, and the optical analysis tool further comprises
a multi-element detector to
receive the processed light from the output ports of the ICE core, and
provide a multi-element detector signal corresponding to a spectrum of the processed light, and
a summing module to
integrate the multi-element detector signal, and
provide an output signal corresponding to a value of the characteristic of the sample.

18. An optical analysis tool comprising:
an integrated computational element (ICE) to
receive, when the tool is operated, light from a sample, and
process at least a portion of the received light, such that the processed light is related, over a processing wavelength range, comprising wavelengths in a range from about 0.2 µm to about 2.5 µm, to a characteristic of the sample,
wherein the ICE comprises
(I) a dispersive optical element comprising
an input port,
a substrate and a planar waveguide disposed on the substrate, the planar waveguide to guide light input through the input port, such that the guided light is within an operational wavelength range, comprising wavelengths in a range from about 0.2 µm to about 2.5 µm, that encompasses the processing wavelength range,
diffractive structures distributed along the planar waveguide to spatially separate the guided light into a plurality of wavelength sub-ranges of the operational wavelength range, wherein a distribution of the diffractive structures is such that the dispersive optical element functions as a spectrograph that weights the respective wavelength sub-ranges of the spatially separated light by substantially equal amounts, and
a plurality of output ports to output the spatially separated light of the respective wavelength sub-ranges; and
(II) an ICE core that weights light incident thereof by differing amounts corresponding to the wavelength sub-ranges within the processing wavelength range, the different amounts being related to the characteristic of the sample, and wherein
the ICE core is optically coupled to the input port of the spectrograph, such that:
the light input to the input port is sample modified light weighted by the ICE core, and
the light output at some of the output ports of the spectrograph (i) is the weighted light spatially separated into the respective wavelength sub-ranges within the processing wavelength range and (ii) represents the light processed by the ICE, and
the optical analysis tool further comprises:
a multi-element detector to
receive the processed light from the output ports of the spectrograph, and
provide a multi-element detector signal corresponding to a spectrum of the processed light, and
a summing module to:
integrate the multi-element detector signal, and
provide an output signal corresponding to a value of the characteristic of the sample, and wherein
the ICE core comprises
a substrate having a first surface, wherein the substrate comprises a substrate material with a substrate material refractive index, and
a plurality of layers stacked on the first surface of the substrate, wherein adjacent ones of the plurality of layers respectively comprise layer materials with refractive indices different from each other, wherein a substrate thickness and thicknesses of the plurality of layers are such that the light weighted by the ICE core is related, over the processing wavelength range, to the characteristic of the sample.

19. An optical analysis tool comprising:
an integrated computational element (ICE) to
receive, when the tool is operated, light from a sample, and
process at least a portion of the received light, such that the processed light is related, over a processing wavelength range, comprising wavelengths in a range from about 0.2 µm to about 2.5 µm, to a characteristic of the sample,
wherein the ICE comprises
(I) a dispersive optical element comprising
an input port,
a substrate and a planar waveguide disposed on the substrate, the planar waveguide to guide light input through the input port, such that the guided light is within an operational wavelength range, comprising wavelengths in a range from about 0.2 µm to about 2.5 µm, that encompasses the processing wavelength range,
diffractive structures distributed along the planar waveguide to spatially separate the guided light into a plurality of wavelength sub-ranges of the operational wavelength range, wherein a distribution of the diffractive structures is such that the dispersive optical element functions as a spectrograph that weights the respective wavelength sub-ranges of the spatially separated light by substantially equal amounts, and
a plurality of output ports to output the spatially separated light of the respective wavelength sub-ranges; and
(II) an ICE core that weights light incident thereof by differing amounts corresponding to the wavelength sub-ranges within the processing wavelength range, the different amounts being related to the characteristic of the sample, and wherein
a refractive index of the planar waveguide's material is larger than a refractive index of the substrate's material, and
the diffractive structures of the dispersive optical element comprise
a first plurality of refractive index altering features extending along a first direction in a plane of the planar waveguide, and a second plurality of refractive index altering features extending along a second direction in the plane, where the second direction is different from the first direction, and a width of the refractive index altering features of the first and second pluralities is selected to cause back scattering of light in respective first and second wavelength sub-ranges.

\* \* \* \* \*